United States Patent
Yao

(10) Patent No.: US 7,027,198 B2
(45) Date of Patent: Apr. 11, 2006

(54) GENERATION AND ANALYSIS OF STATE OF POLARIZATION USING TUNABLE OPTICAL POLARIZATION ROTATORS

(75) Inventor: X. Steve Yao, Diamond Bar, CA (US)

(73) Assignee: General Photonics Corporation, Chino, CA (US)

(*) Notice: Subject to any disclaimer, the term of this patent is extended or adjusted under 35 U.S.C. 154(b) by 0 days.

(21) Appl. No.: 10/914,592

(22) Filed: Aug. 9, 2004

(65) Prior Publication Data

US 2005/0200941 A1 Sep. 15, 2005

Related U.S. Application Data

(63) Continuation-in-part of application No. 10/800,406, filed on Mar. 12, 2004.

(60) Provisional application No. 60/493,880, filed on Aug. 8, 2003, provisional application No. 60/578,700, filed on Jun. 10, 2004.

(51) Int. Cl.
*G02F 1/03* (2006.01)
*G02F 1/09* (2006.01)
*G01J 4/00* (2006.01)

(52) U.S. Cl. .................. 359/259; 359/280; 356/368

(58) Field of Classification Search ............... 359/250, 359/259, 279, 280, 301, 303; 356/364, 367, 356/368
See application file for complete search history.

(56) References Cited

U.S. PATENT DOCUMENTS

| | | | |
|---|---|---|---|
| 6,417,948 B1 * | 7/2002 | Chowdhury et al. | 398/158 |
| 6,493,474 B1 | 12/2002 | Yao | |
| 6,542,650 B1 | 4/2003 | Khosravani et al. | |
| 6,643,064 B1 * | 11/2003 | Huang et al. | 359/497 |

* cited by examiner

*Primary Examiner*—Georgia Epps
*Assistant Examiner*—William Choi
(74) *Attorney, Agent, or Firm*—Fish & Richardson P.C.

(57) ABSTRACT

This application describes optical monitoring devices and applications in optical systems for monitoring various optical parameters of light, including the signal to noise ratio, the degree of polarization, and the differential group delay (DGD).

28 Claims, 21 Drawing Sheets

Wavelength

US 7,027,198 B2

GENERATION AND ANALYSIS OF STATE OF POLARIZATION USING TUNABLE OPTICAL POLARIZATION ROTATORS

This application claims the benefits of:

U.S. Provisional Patent Application No. 60/493,880 entitled "SOP Generator and Analyzer Based on Tunable Optical Polarization Rotators" and filed Aug. 8, 2003 ; and U.S. Provisional Patent Application No. 60/578,700 entitled "Generation and Analysis of State of Polarization Using Tunable Optical Polarization Rotators" and filed Jun. 10, 2004.

In addition, this application is a continuation-in-part application of and claims the benefit of U.S. patent application Ser. No. 10/800,406 entitled "Monitoring Mechanisms for Optical Systems" and field Mar. 12, 2004.

The entire disclosures of the above three referenced applications are incorporated herein by reference as part of the specification of this application.

BACKGROUND

This application relates to optical polarization devices and their applications including polarization-based optical monitoring devices and systems.

Optical properties or parameters of light in an optical device or system may be measured for various purposes. As an example, such an optical measurement may be used to determine the performance or an operating condition of the device or system. An optical property or parameter of light under measurement may include the optical polarization, the signal to noise ratio, the differential group delay between two orthogonal polarization states, and others.

The optical polarization is an important parameter of an optical signal in various optical systems. For example, in fiber optic communication systems, polarization-dependent effects in fibers and other devices, such as polarization-dependent loss (PDL) and polarization-mode dispersion (PMD), can have significant impacts on performance and proper operations of optical devices or systems. Hence, it may be desirable to measure and monitor the state of the polarization (SOP) and the degree of polarization (DOP) of an optical signal in these and other systems.

Similarly, the signal-to-noise ratio (SNR) and the differential group delay (DGD) of an optical signal are also important parameters for various optical devices and systems and hence monitoring of these parameters may be desirable under certain circumstances.

SUMMARY

This application includes various implementations and examples of devices and techniques for monitoring the SNR, DOP, and DGD of one or more optical signals. In one implementation, an optical scrambler and a polarizer may be used in the optical path for the measurements. In another implementation, a rotatable quarter waveplate and a rotatable half waveplate are used in the optical path for the measurements. In yet another implementation, a state-of-polarization generator and a linear polarizer may be used for the measurements. The optical monitoring devices described here may be used to measure WDM channels.

One example of devices described here includes first and second polarization rotators sequentially positioned in an optical path, a quarter waveplate in the optical path to receive output light from the first and second polarization rotators, and third and fourth polarization rotators sequentially positioned in the optical path to receive output light from the quarter waveplate. Each polarization rotator is adjustable in response to a control signal and may be operate at two binary rotation angles.

In another example, a device includes at least four polarization rotators positioned in an optical path and each polarization rotator is adjustable in response to a control signal to rotate the polarization by either +22.5° or −22.5°. The device also includes a quarter wave plate in said optical path.

Methods for generates states of polarization and analyzing polarization are also described here. One example of such described methods uses at least four polarization rotators and a quarter wave plate in an optical path to transmit light. each polarization rotator is controlled to rotate polarization by two different predetermined angles. The at least four polarization rotators are controlled to operate in different rotator settings and to generate at least four different states of polarization.

These and other implementations and applications are described in greater detail in the attached drawings, the detailed description, and the claims.

DETAILED DESCRIPTION

Figure 1:
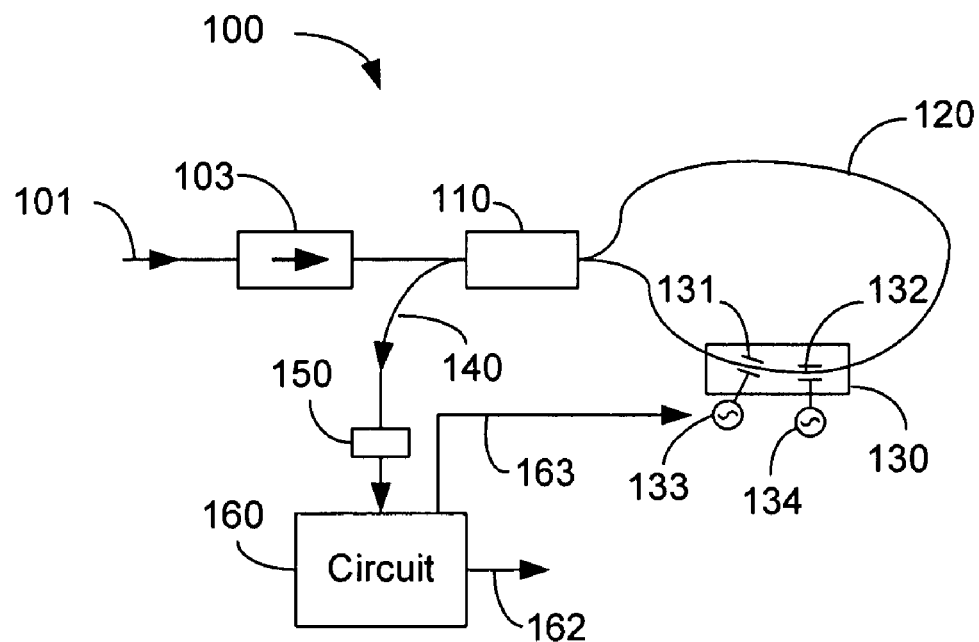
FIGS. 1 and 2 show two exemplary optical monitoring devices with a polarization scrambler or controller.

FIG. 1 illustrates one exemplary implementation of a monitoring device 100 for monitoring both SNR and DOP in the received light. The monitoring device 100 may use a fiber to receive an optical signal 101 under monitoring, and an optical loop 120 such as a fiber loop to perform the monitoring. An optical coupler 110, such as a 50% fiber coupler, may be coupled to the two ends of the fiber loop 120 to split the input signal 101 into two counter-propagating beams in the loop 120 and to combine the two counter-propagating beams to produce an output beam 140. Hence, the coupler 110 and the loop 120 provides a mirroring mechanism. A polarization scrambler or controller 130 is placed in the fiber loop 120 to either randomly scramble the polarization of light in the loop 120 or to systematically control the polarization to vary through all possible states of polarization so that a maximum power level and a minimum power level in the output beam 140 can be obtained and measured. The polarization scrambler or controller 130 may be optionally controlled in response to a control signal 163 to adjust the state of polarization of light passing therethrough.

In one implementation of the device 130 as illustrated in FIG. 1, the polarization scrambler or controller 130 may include two or more fiber squeezers 131 and 132 respectively under control of the controllers 133 and 134. The squeezing directions of the fiber squeezers 131 and 132 are oriented to be 45 degrees with respect to each other to perform the scrambling operations.

An optical detector 150 may be coupled to receive the output light 140 from the loop 120. An optional optical isolator 103 may be placed in the path of the input beam 101 to prevent any optical feedback to the input path. A processing circuit 160 is coupled to receive the detector output from the detector 150 to produce an output signal 162 which includes information about the SNR or DOP.

In operation, the detector 150 detects the maximum and the minimum optical power levels in the output signal 140. The processing circuit 160 can be designed to compute the extinction ratio. based on measured maximum and the minimum optical power levels. In various applications, the signal 101 is generally polarized and the noise is not polarized. Hence, the extinction ratio can directly relate to the SNR and DOP. As the extinction ratio increases, the DOP and the SNR increase accordingly, and vice versa. The processing circuit 160 may also includes a control unit that controls the operation of the polarization scrambler 130.

Figure 2:
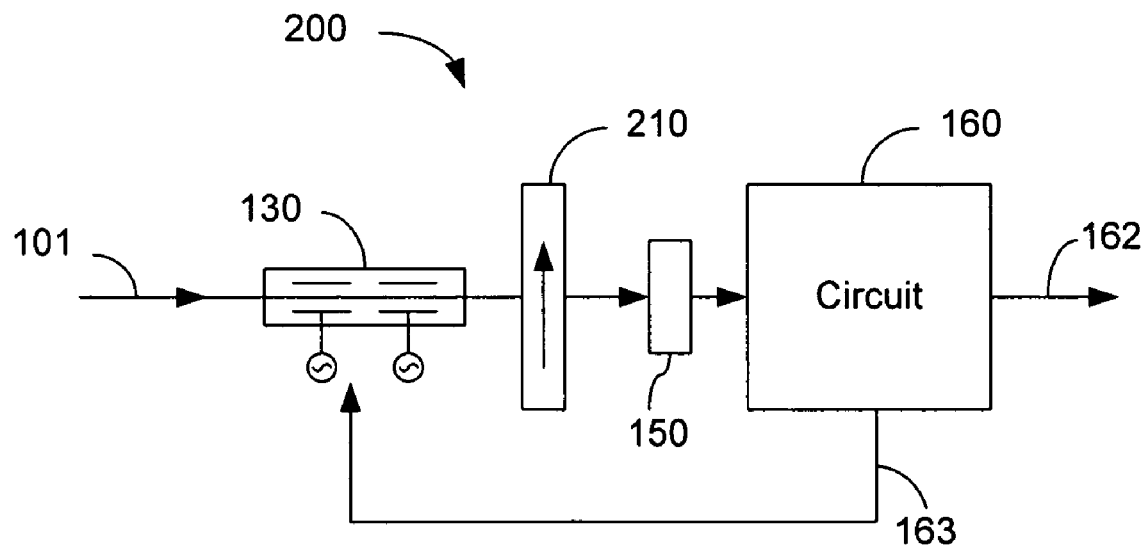

FIG. 2 shows a monitoring device 200 based on another implementation. The polarization scrambler 130 is used to scramble the input light 101 and a polarizer 210 is used to transmit the output light of the scrambler 130. The polarizer 210 is used here to replace the mirroring loop 120 in the monitoring device 100 in FIG. 1. The optical detector 150 is then used to receive the transmitted light from the polarizer 210. The processing circuit 160 receives and processes the detector output to produce the output 162.

Figure 3:
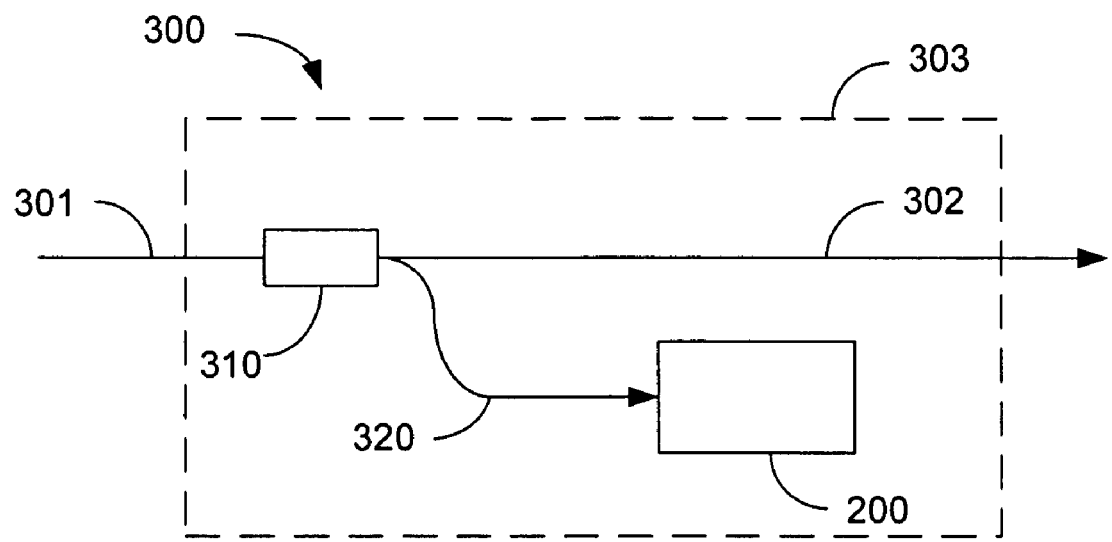
FIG. 3 shows an implementation of the monitoring device in FIG. 2 in a transmission system.

FIG. 3 shows an implementation of the monitoring device 200 in a transmission system 300. An optical coupler 310 is placed in the path of the input beam 301 to tap a fraction of the input 301 as a monitoring beam 320 and the remaining 302 of the input 301 continues along the input path as an output of the system 300. The monitoring device 200 is coupled to receive the monitoring beam 320 to perform the measurement. Notably, a housing 303 may be used to enclose the coupler 310, the path for, the monitoring beam 320, and the monitoring device 200. All optical paths may be fibers, dielectric waveguides, or a combination of fiber paths and waveguide paths. The housing may be hermetically sealed to provide an integrated package for deployment in a fiber transmission line or system. A substrate may be used to fabricated waveguides and other optical components in a single-chip package enclosed within the housing 303. It is understood that, the monitoring device 100 in FIG. 1 may also be used to replace the device 200 in FIG. 3 and other systems shown in this application.

Figure 4:
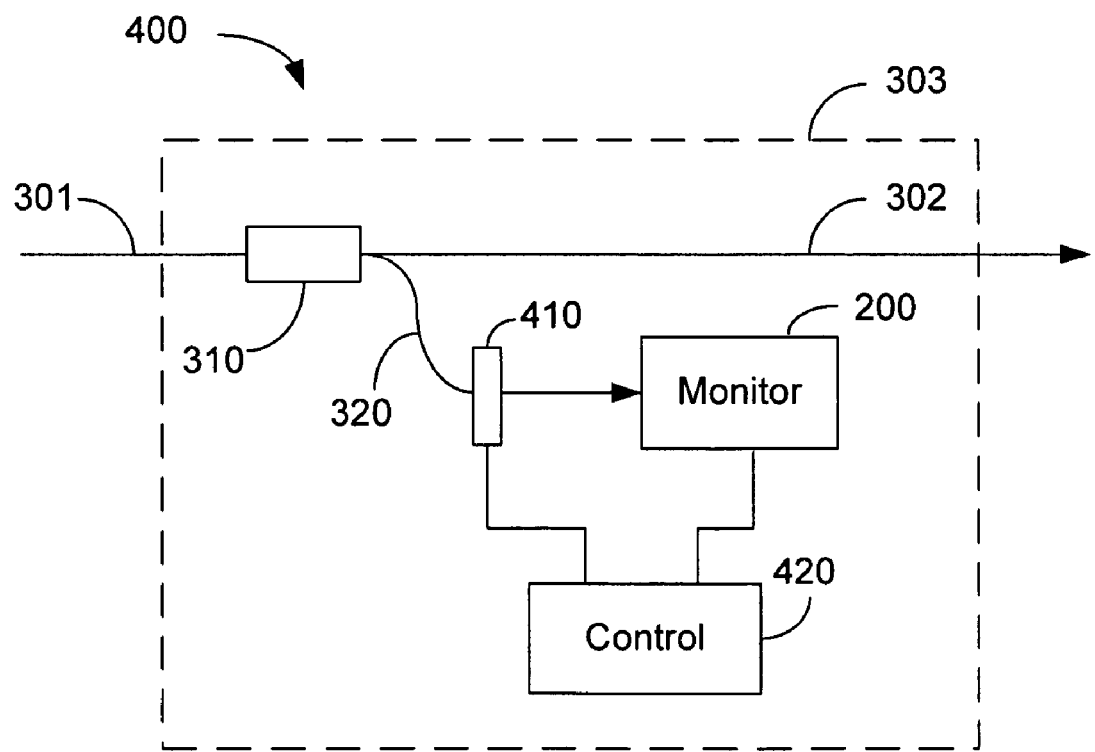
FIG. 4 shows a monitoring setup for a wavelength-division-multiplexed (WDM) transmission line where the input includes signals at different WDM wavelengths.

FIG. 4 shows a monitoring setup for a wavelength-division-multiplexed (WDM) transmission line where the input 301 includes signals at different WDM wavelengths. The coupler 310 may split all WDM signals at the input to produce the monitoring beam 320. A WDM coupler may be used as the coupler 310. A tunable optical filter 410 is coupled between the coupler 310 and the monitoring device 200 or 100 to sequentially filter the WDM signals so that only one signal at a single WDM wavelength is transmitted to the device 200 or 100. As the filter 410 is tuned sequentially through all signal wavelengths, one at a time, each and every WDM signal is measured by the device 200 or 100. A control device 420 may be implemented and coupled to the filter 410 and the monitoring device 200 or 100 to control such sequential filtering and monitoring operations. The tunable filter 410 may be implemented in a number of configurations, such as a tunable Fabry-Perot filter, a tunable fiber grating filter (e.g., coupled with a fiber stretcher), multiple filters with different transmission wavelengths on a rotation wheel which may be controlled by a step motor, and others.

Figure 5:
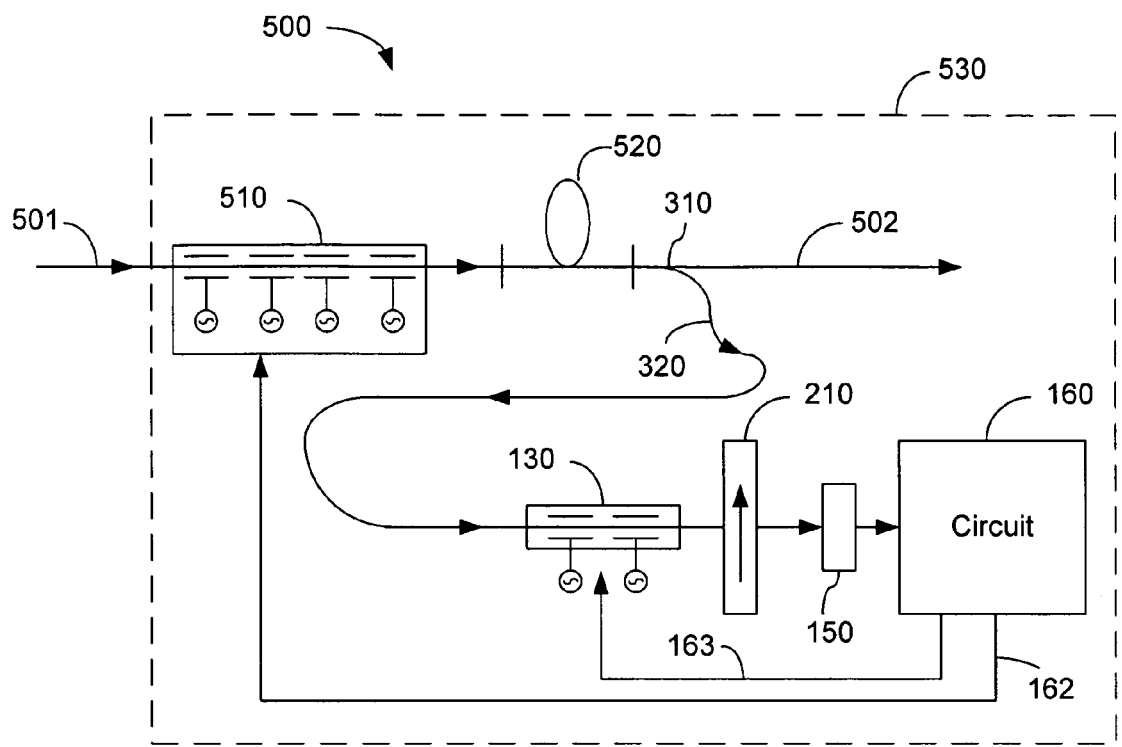
FIG. 5 shows one implementation of an all-fiber dynamic PMD controller 500 based on the above monitoring techniques.

FIG. 5 shows one implementation of an all-fiber dynamic PMD controller 500 based on the above monitoring techniques. An adjustable polarization controller 510 is coupled in the input fiber to control the polarization of the input beam 501. A polarization-maintaining fiber segment 520 is coupled to the output of the polarization controller 510 to produce the desired differential group delay in the output light from the controller 510. Fiber fusion splicing may be used to connect the PM fiber segment 510. A fiber coupler 310 is used to split the output of the controller 510 into an output beam 502 in the input fiber and a monitoring beam 320 to the monitoring device 200 in FIG. 2 (or the device 100 in FIG. 1) for monitoring the degree of polarization. The circuit 160 is coupled to supply the output 162 to control the polarization controller 510 so that the polarization controller 510 can be dynamically adjusted in response to the measurement by the circuit 160. The polarization controller 510 may be implemented in various configurations. The PMD controller 500 may include multiple, e.g., three or more, fiber squeezers. U.S. Pat. No. 6,493,474 granted to Yao on Dec. 10, 2002 discloses some examples based on four sequential fiber squeezers and is incorporated herein in its entirety as part of the specification of this application.

The system in FIG. 5 may be used to achieve a number of advantages, such as low optical loss at less than 0.5 dB and low cost due to the unique designs based on simple optical layout and simple components. A hermetically-sealed housing 530 may be implemented as illustrated.

Figure 6:
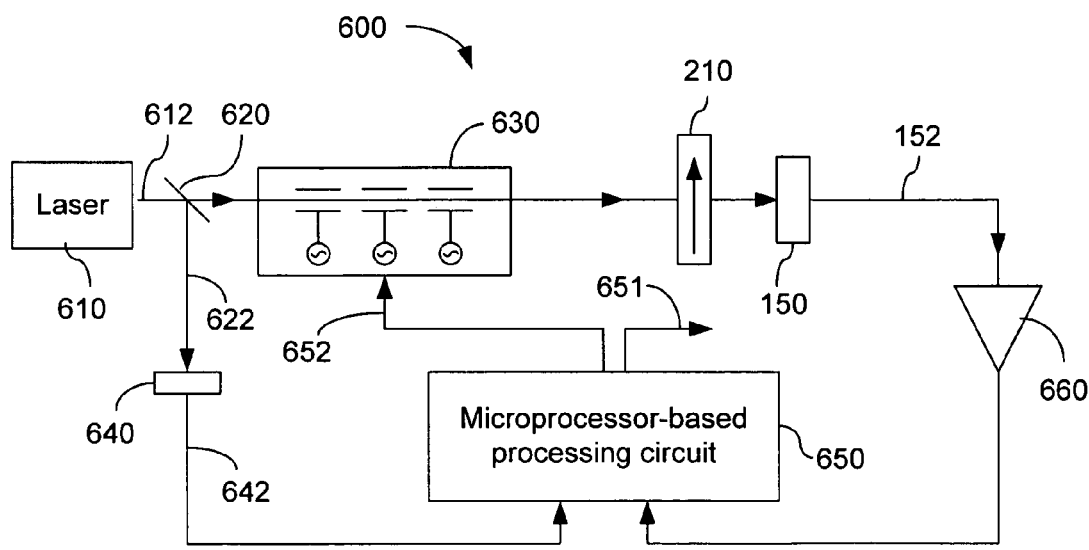
FIG. 6 shows one implementation of a microprocessor-based monitoring device.

FIG. 6 shows one implementation of a microprocessor-based monitoring device 600. A polarization controller 630 is used to adjust the SOP of the input light 612 under monitoring and a polarizer 210 is used to transmit the output light of the controller 630 to an optical detector 150. The output signal 152 from the detector 150 may be electrically amplified by an amplifier 660 and the amplified signal is sent to a microprocessor-based processing circuit 650. The processing circuit 650 converts each received analog signal into digital bits and performs the signal processing operations by using a microprocessor in the digital domain. An output 651 is then produced to indicate the monitoring result on either the DOP or the SNR of the light 612. As illustrated, a laser 610 or other light source may be used to produce the input light 612.

Optionally, a beam splitter 620, such as a fiber coupler, may be used to split a fraction of the input beam 612 as a reference beam 622 to a second optical detector 640. This beam splitter 620 should be insensitive to the light polarization. The output 642 of the second detector 640 is then fed into the circuit 650 for processing. This reference beam 622 provides a measurement of the power variation in the input beam 612 so that a part of the variation in the received signal 152 caused by the power variation alone may be deducted from the variation caused by the polarization change caused by the scrambler 630.

In operation, the circuit 650 may produce a control signal 652 to adjust the controller 630 in search for the maximum power ($V_{max}$) and the minimum power ($V_{min}$) at the detector 150. The control signal 652 may be digitally generated by the microprocessor and then converts into an analog signal. Based on measurements on the Vman and Vmin, the processor in the circuit 650 computes the DOP or SNR of the light. The DOP may be computed as follows:

$$DOP = \frac{V_{max} - V_{min}}{V_{max} + V_{min}}.$$

The polarization controller 630 may use a two-squeezer design as the element 130 in FIG. 1 or a three-squeezer design as illustrated in FIG. 6, or five- or six-squeezers to provide increased control in adjusting the SOP of input light.

FIG. 6 shows a termination design where the input beam is entirely used for the monitoring operation. Alternatively, the monitoring device 600 may be implemented as an in-line package similar to the design in FIG. 3 where an additional splitter 310 is used to split the main input beam 301 to produce the input to the monitoring device 600 and the remaining of the main input beam continues to propagate in the transmission system.

In the above and other monitoring devices in this application, a tunable optical filter may be inserted in the input path to allow for sequential monitoring of different WDM channels in the input. FIG. 4 shows one example. This multi-channel technique based on a tunable filter can be implemented in various monitoring devices of this application. However, this technique is limited to sequential monitoring of one channel at a time.

Figure 7:
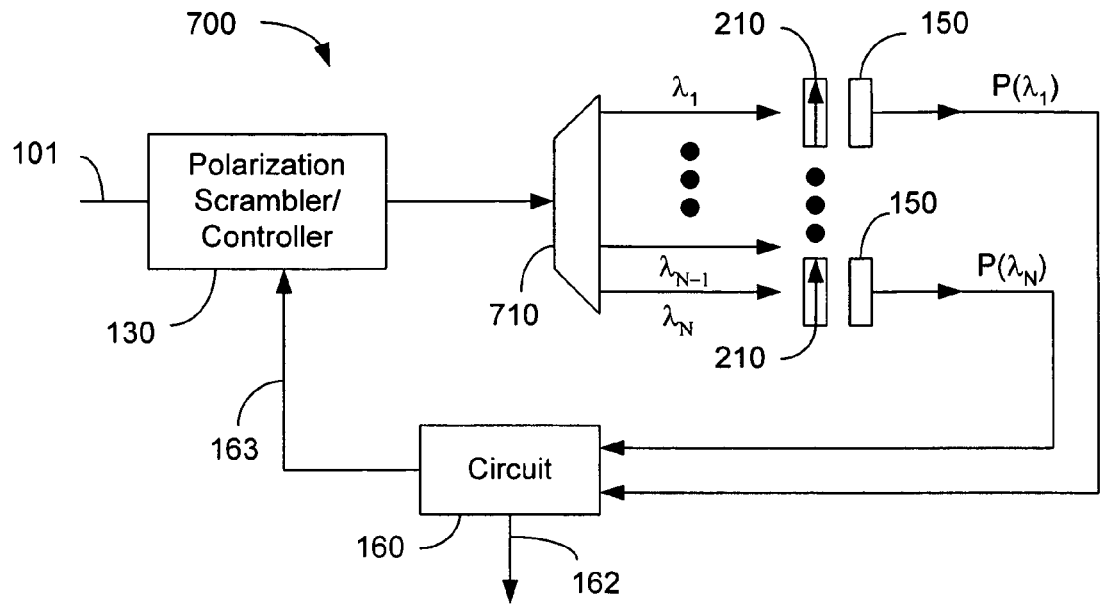
FIG. 7 shows a monitoring device that uses a WDM demultiplexer in the output of the polarization scrambler or controller to separate different WDM channels.
Figure 8:
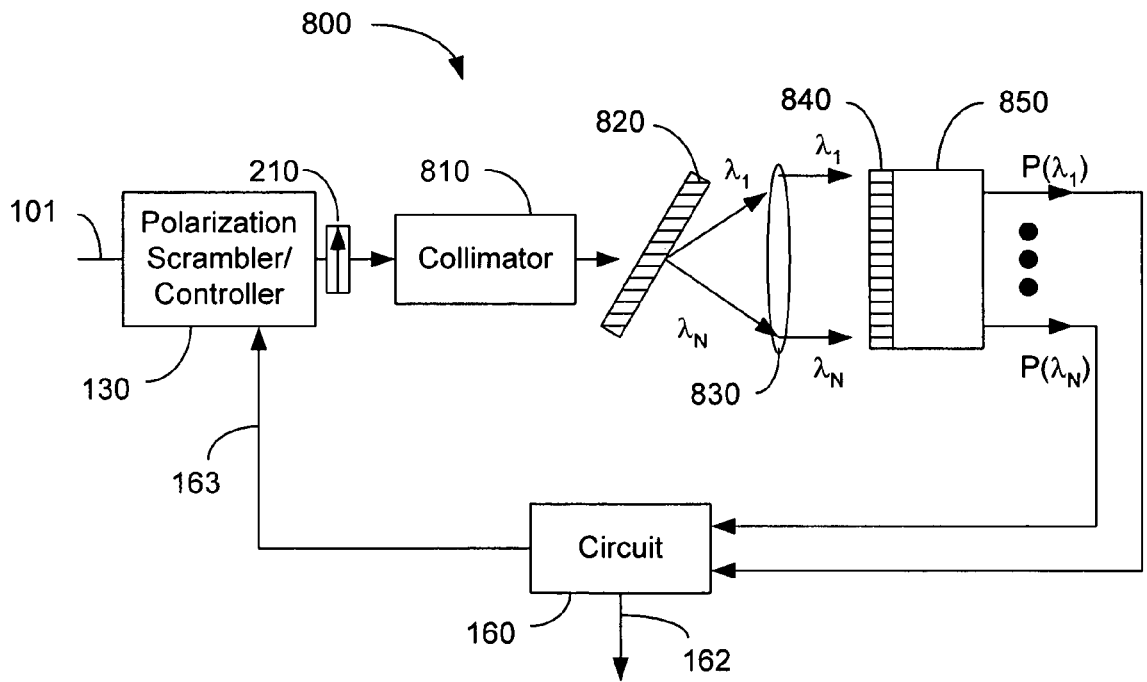
FIG. 8 shows another implementation where a diffraction grating is used to separate different WDM channels.

FIGS. 7 and 8 illustrate two multi-channel monitoring techniques for simultaneous monitoring of different WDM channels. Such techniques allows for taking snap shots of different channels at the same time.

FIG. 7 shows a monitoring device 700 that uses a WDM demultiplexer 710 in the output of the polarization scrambler or controller 130 to separate different WDM channels. In the optical path of each separate WDM channel, a polarizer 210 and an optical detector 150 are used to receive and detect the power levels of each channel. Hence, power levels of different channels can be measured at the same time. The output signals from the detectors 150 are then fed into the circuit 160 for data processing to monitor the WDM channels. Multiple polarizers 210 are placed in the optical paths between the dmux 710 and the detectors 150. Alternatively, a single polarizer may be placed between the polarization scrambler 130 and the WDM demultiplexer 710 to replace with multiple polarizers 210 in front of the detectors 150.

FIG. 8 shows another implementation 800 where a diffraction grating 820 is used to separate different WDM channels. A collimator 810 is used to receive the output of the polarization scrambler 130 to produce a collimated output. A polarizer 210 is placed between the polarization scrambler 130 and the collimator 810. The grating 820 diffracts the input light at different WDM wavelengths at different diffraction angles. This diffraction spatially separates different WDM channels. A second collimator 830, such as a lens, is used to collect the diffracted beams of different channels and focus the diffracted beams onto different detector elements of an array of optical detectors 840. A processing circuit 850 may be optionally used to condition the detector output signals prior to the circuit 160.

The above monitoring devices based on a polarization scrambler may be sensitive to the PMD in the input signal that includes two or more WDM channels. This sensitivity on the PMD may cause an error in the measurement. In general, the greater the PMD in the input, the larger the error of the monitoring device. Hence, it may be desirable to mitigate this PMD effect in monitoring the DOP or SNR.

Figure 9:
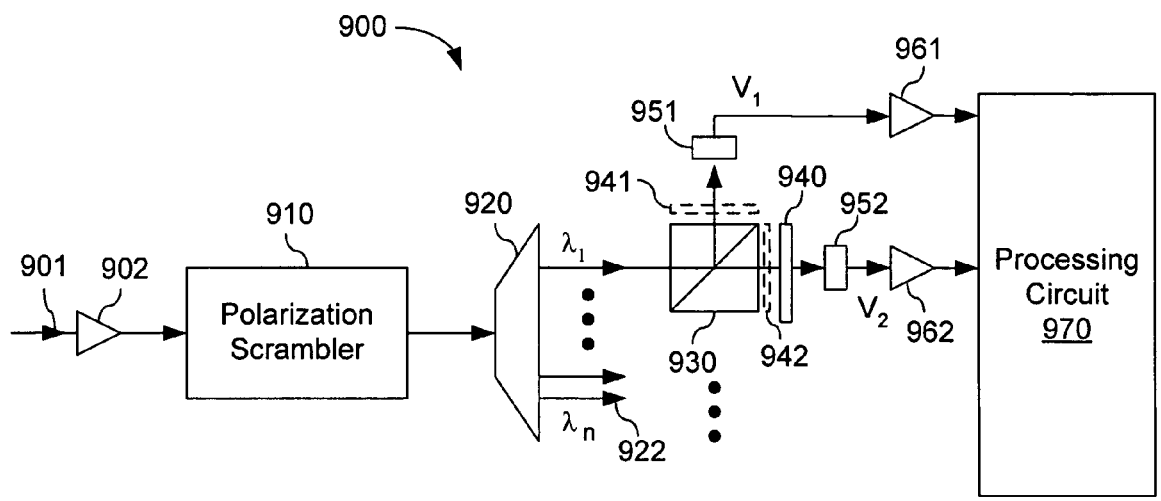
FIG. 9 shows one implementation of a PMD-insensitive monitoring device for WDM applications where only a single polarization scrambler is used for all wavelength channels.

FIG. 9 shows one implementation of a PMD-insensitive monitoring device 900 for WDM applications where only a single polarization scrambler is used for all wavelength channels. The device 900 includes a universal polarization scrambler 910 to receive input WDM channels in an input fiber 901. One or more optical amplifiers 902 may be used in the input optical path to amplify the input WDM channels. A WDM demultiplexer 920 is used to receive the output from the scrambler 910 and to split different WDM channels by their wavelengths as separate optical output signals 922. In each optical output, a polarizing beam splitter (PBS) 930 or a suitable polarization device is used to split the received light based on their two orthogonal polarizations to produce two beams with orthogonal polarizations. A bandpass filter 940 is used to filter one of the two outputs of the PBS 930 so that the power levels of the noise power levels in two output beams are different while the power levels of the signals in the output beams are essentially unaffected by the filtering. As illustrated, the filter 940 may be positioned to filter light from the port that transmits light along the direction of the input beam.

The above optical filtering causes an imbalance between the noise power levels in the two output beams with orthogonal polarizations. This imbalance is used for simultaneous and independent monitoring of both SNR and DOP. Two orthogonally oriented polarizers 941 and 942 may be optionally placed at the two output ports of the PBS 941 to ensure the output beams are orthogonally polarized. Two optical detectors 951 and 952 are positioned to receive the two outputs of the PBS 930, respectively. The output signals of the detectors 951 and 952 are fed into a processing circuit 970 for measurements and data processing. Two electrical signal amplifiers 961 and 962 may be optionally used to amplify the detector outputs, respectively, prior to the processing by the circuit 970.

In one implementation, the bandpass filter 940 may have a bandwidth broader than the actual bandwidth of each signal channel to allow each signal channel to pass without filtering but narrower than the bandwidth of the WDM device for each channel to filter out some noise components to create the power imbalance in the noise between the two output beams. For example, for WDM channels with 100 GHz in the channel spacing and 10 GHz in the channel bandwidth, the WDM demultiplexer 920 may be designed to have a channel bandwidth of 50 GHz. The bandpass filter 940 may have a bandwidth of 25 GHz, between the 10-GHz channel bandwidth and 50-GHz device channel bandwidth, to allow a channel to pass through without being filtered. However, the noise components outside the 25 GHz window are filtered out in the transmitted beam of the PBS 930.

The maximum and minimum detected power of all SOP detected at the two detectors 951 and 952 are:

$$\begin{cases} V_1^{max} = G_1[P_s(1-\delta) + 0.5P_N] & (1) \\ V_1^{min} = G_1[P_s\delta + 0.5P_N] & (2) \\ V_2^{max} = G_2[P_s(1-\delta) + 0.5\alpha P_N] & (3) \\ V_2^{min} = G_2[P_s\delta + 0.5\alpha P_N] & (4) \end{cases}$$

where $P_S$ is the signal power, $P_N$ is the noise power, $\alpha$ is less than 1 and is the noise power filtering factor of the bandpass filter 940, and $\delta$ the depolarization factor caused by, e.g., the PMD in the input signal, the nonlinear birefringence, and imperfection of the PBS 930. Notably, in absence of the filter 940 which produces the an inbalance between the two output beams from PBS 930, the Eqs. (1) and (2) would be identical to Eqs.(3) and (4). The filter 940 is specifically used to break the degeneracy and to provide separate measures of SNR and DOP.

Equations (1) and (2) are added to obtain the following:

$$V_1^{max} + V_1^{min} = G_1(P_S + P_N) \tag{5}$$

Equations (1) and (2) are subtracted:

$$V_1^{max} - V_1^{min} = G_1 P_S(1-2\delta) \tag{6}$$

Similar manipulations of Equations (3) and (4) yield:

$$V_2^{max} + V_2^{min} = G_2(P_S + \alpha P_N) \tag{7}$$

$$V_2^{max} - V_2^{min} = G_2 P_S(1-2\delta) \tag{8}$$

Additionally, the following signal processing can be carried out:

$$G_2 \cdot Eq.(5) - G_i \cdot Eq.(7) = G_2(V_1^{max} + V_1^{min}) - G_1(V_2^{max} + V_2^{min})$$
$$= G_1 G_2 P_s + G_1 G_2 P_N - G_1 G_2 P_s -$$
$$\alpha G_1 G_2 P_N.$$

Hence, the following can be obtained:

$$G_1 G_2(1-\alpha)P_N = G_2(V_1^{max} + V_1^{min}) - G_1(V_2^{max} + V_2^{min}), \text{ and} \tag{9}$$

$$P_N = \frac{1}{1-\alpha}\left[\frac{V_1^{max} + V_a^{min}}{G_1} - \frac{V_2^{max} + V_2^{min}}{G_2}\right]$$

From Eq.(5), the following can be derived:

$$G_1 P_s = (V_1^{max} + V_1^{min}) - G_1 P_N$$
$$= (V_1^{max} + V_1^{min}) - \frac{1}{1-\alpha}\left[(V_1^{max} + V_1^{min}) - \frac{G_1}{G_2}(V_2^{max} + V_2^{min})\right]$$
$$= \left(1 - \frac{1}{1-\alpha}\right)(V_1^{max} + V_1^{min}) + \frac{G_1/G_2}{1-\alpha}(V_2^{max} + V_2^{min})$$
$$= \frac{1}{1-\alpha}\left[\frac{G_1}{G_2}(V_2^{max} + V_2^{min}) - \alpha(V_1^{max} + V_1^{min})\right].$$

Therefore, the following expressions can be derived:

$$P_s = \frac{1}{1-\alpha}\left[\frac{V_2^{max} + V_2^{min}}{G_2} - \frac{\alpha}{G_1}(V_1^{max} + V_1^{min})\right] \tag{10}$$

$$S/N = \frac{P_s}{P_N}$$
$$= \frac{\frac{V_2^{max} + V_2^{min}}{G_2} - \frac{\alpha}{G_1}(V_1^{max} + V_1^{min})}{\frac{V_1^{max} + V_1^{min}}{G_1} - \frac{V_2^{max} + V_2^{min}}{G_2}}$$
$$= \frac{G_1(V_2^{max} + V_2^{min}) - \alpha G_2(V_1^{max} + V_1^{min})}{G_2(V_1^{max} + V_1^{min}) - G_1(V_2^{max} + V_2^{min})}.$$

Let $\bar{V}_1 = \frac{1}{2}(V_1^{max} + V_1^{min})$, and $\bar{V}_2 = \frac{1}{2}(V_2^{max} + V_2^{min})$, the SNR can be computed as follows:

$$\frac{S}{N} = \frac{G_1 \bar{V}_2 - \alpha G_2 \bar{V}_1}{G_2 \bar{V}_1 - G_1 \bar{V}_2}. \tag{12}$$

if $G_1=G_2$, then SNR becomes $$\frac{S}{N} = \frac{\overline{V}_2 - \alpha \overline{V}_1}{\overline{V}_1 - \overline{V}_2}.$$

Hence, the signal to noise ratio only depends on the average $V_1$ and $V_2$. This approach essentially excludes all the effects of PMD, the nonlinear birefringence, and the PBS imperfection.

From Equations (6), (9), and (10), the depolarization factor δ can be calculated as:

$$G_1 P_s (1 - 2\delta) = V_1^{max} - V_1^{min},$$

$$1 - 2\delta = \frac{1}{G_1 P_s}(V_1^{max} - V_1^{min}), \text{ and}$$

$$\delta = \frac{1}{2}\left[1 - \frac{1}{G_1 P_s}(V_1^{max} - V_1^{min})\right]$$

$$= \frac{1}{2}\left[1 - \frac{(1-\alpha)(V_1^{max} - V_1^{min})}{\frac{G_1}{G_2}(V_2^{max} + V_2^{min}) - \alpha(V_1^{max} + V_1^{min})}\right].$$

For $G_1=G_2$, the depolarization factor can be simplified as:

$$\delta = \frac{1}{2}\left[1 - \frac{(1-\alpha)(V_1^{max} - V_1^{min})}{2(\overline{V}_2 - \alpha\overline{V}_1)}\right].$$

The contribution to δ from the imperfection of the PBS 930 can be eliminated by placing polarizers 941 and 942 at the outputs of the PBS 930 in FIG. 9. Accordingly, the depolarization caused by PMD can be precisely measured. This mechanism may also be used to monitor the PMD effect.

Figure 10:
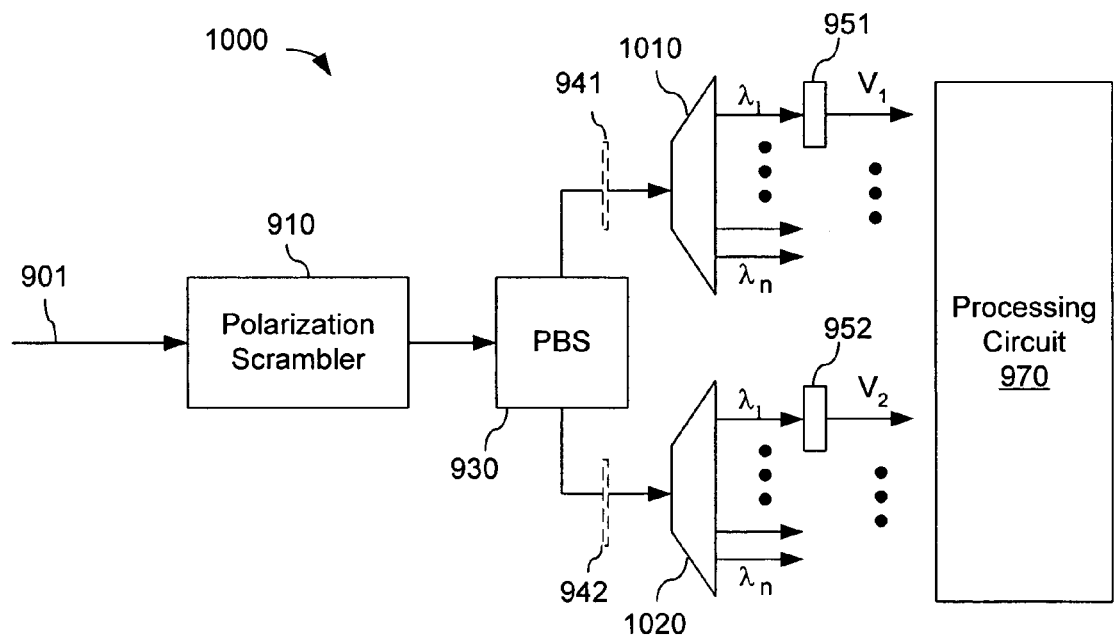
FIG. 10 shows another implementation of a WDM monitoring device where a single polarization beam splitter is combined with two WDM demultiplexers.

The device in FIG. 9 uses multiple PBSs for the separated WDM channels. Alternatively, FIG. 10 shows another implementation 1000 where a single PBS 930 is combined with two WDM demultiplexers 1010 and 1020. In this design, the two demultiplexers 1010 and 1020 may be purposely designed to be different to introduce the noise power imbalance with a factor of α(λi) (i=1, 2, . . . , N). For example, the device channel bandwidths of the two demultiplexers 1010 and 1020 may be different, e.g., one is 50 GHz and the other is 75 GHz for WDM signals with a channel bandwidth of 10 GHz and a channel spacing of 100 GHz, where each WDM channel transmits without being attenuated but the noise power levels of the same channel in the outputs of the demultiplexers 1010 and 1020 are different. Hence, the filter 940 in FIG. 9 may be eliminated. If the two demultiplexers 1010 and 1020 are identical, then the filtering is needed to introduce the power imbalance.

Figure 11:
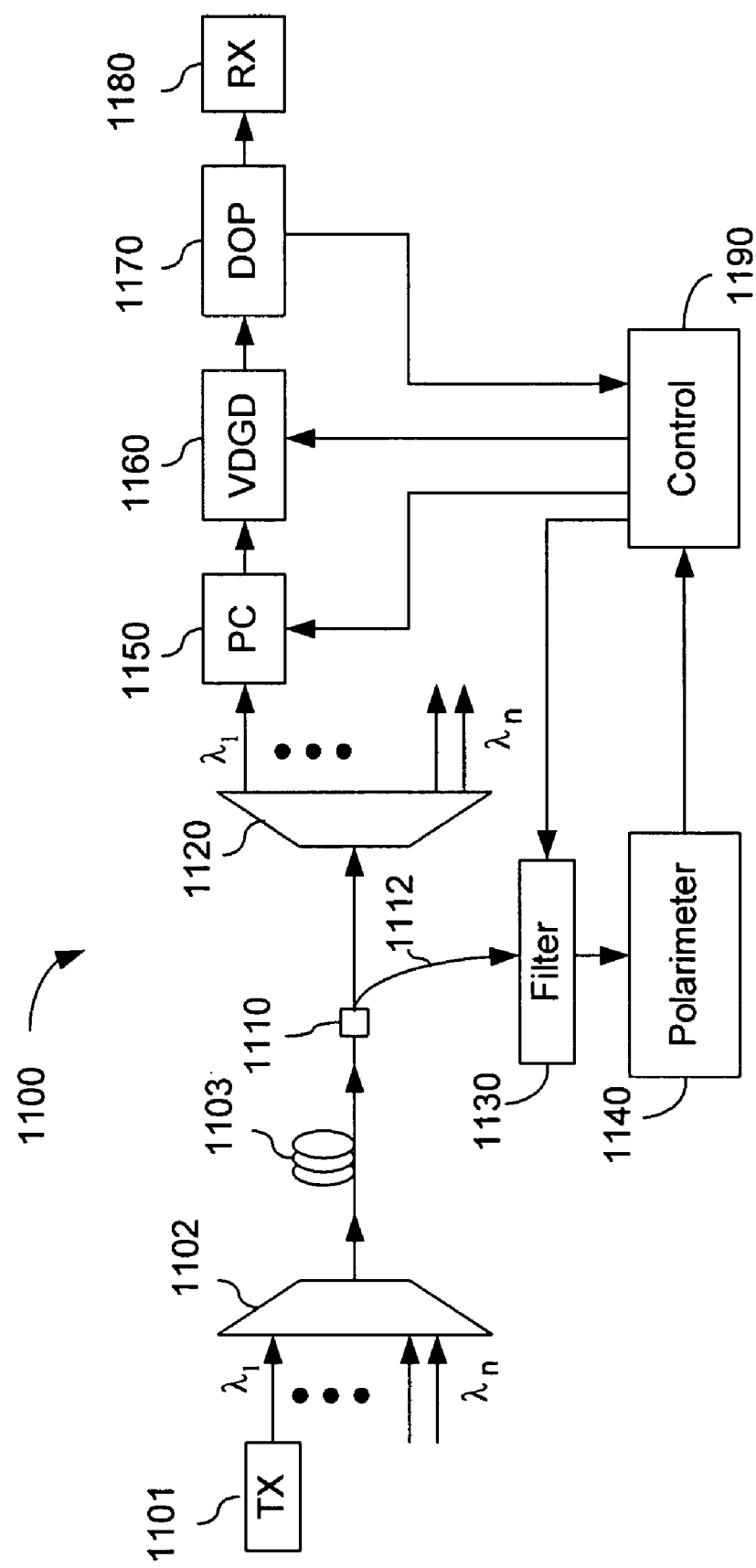
FIG. 11 shows a system having a real-time DGD monitoring device and a dynamic PMD compensator.

Now turning to FIG. 11, a real-time DGD monitoring mechanism is shown in the fiber system 1100 and is used in connection with a dynamic PMD compensator. The fiber system includes three main modules: a transmitter terminal, the fiber transmission line 1103 which may include a fiber link with optical amplifiers, and a receiving terminal. The transmitter terminal may include multiple optical transmitters 1101 at different channel wavelengths and a WDM multiplexer 1102 to multiplex the different channels for transmission in the fiber link 1103. The receiving terminal includes a DGD monitor, a demultiplexers 1120, dynamic PMD compensators for different channels, and optical receivers 1180 for different channels. An optical coupler 1110, such as a fiber coupler, may be placed in the input of the demultiplexer 1120 to split a fraction of the input signal as a monitor beam 1112 to the DGD monitor and the main input signal is received by the demultiplexer 1120.

The DGD monitor in the system 1100 includes a tunable filter 1130, a polarimeter 1140, and a DGD processing circuit within a control unit 1190. The filter 1130 is tuned to sequentially scan through different WDM or DWDM channels to allow for different channels to reach the polarimeter 1140, one at a time. The bandwidth of the filter 1130 is sufficiently narrower than the bandwidth of each channel. The polarimeter 1140 is operable to measure the SOP at a high speed for the real-time monitoring. The DGD processing circuit within the control unit 1190 receives and processes the SOP signal generated by the polarimeter 1140 to determine the DGD in each channel.

In operation, the tunable filter 1130 is tuned to a channel at its center wavelength λi and is scanned around λi for a duration longer than the time for the polarimeter 1140 to measure the SOP of that channel. During this scanning around λi, the polarimeter processes the input optical signal at λi to produce the information on the SOP of this channel.

Figure 12:
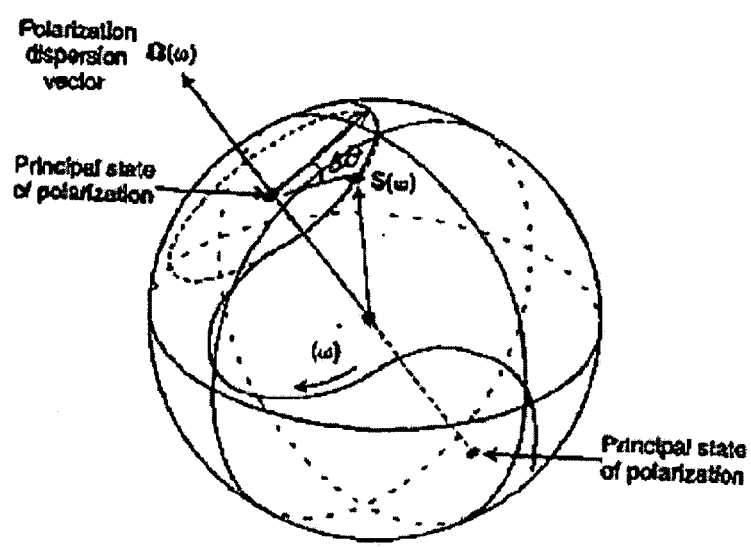
FIG. 12 illustrates the processing operation by a DGD processing circuit in FIG. 11 with reference to the Poincare sphere for the polarization.

FIG. 12 illustrates the processing operation by the DGD processing circuit with reference to the Poincare sphere for the polarization. Let the angular variation in the SOP angle around the principal axis Ω be Δθi for the channel λi, and the frequency tuning range around the center wavelength λi be Δf i, the DGD can be calculated as follows:

$$\Delta \tau_i = \frac{\Delta \theta_i}{2\pi \Delta f_i}.$$

This calculation is performed by the DGD processing circuit. FIG. 12 shows that, both the DGD and direction of the principal axis Ω can be determined.

Next, the control unit 1190 uses the DGD information to control the PMD compensator to produce a DGD that negates this measured DGD. This completes the monitoring and control operation on one channel. The control unit 1190 then commands the filter 1130 to tune to the next channel to repeat the monitoring and compensation operation. This process repeats for all channels sequentially.

The DGD monitoring mechanism in FIG. 11 is shared by all channels. The PMD compensation, however, is implemented individually for each channel. Hence, multiple PMD compensators are used in the example in FIG. 11 for different channels, respectively. Only one compensator for the channel λ1 is depicted for simplicity.

In the optical path for each channel after the demultiplexer 1120, the PMD compensator for that channel is placed before a respective channel receiver 1180. The PMD compensator may include an optical polarization controller (PC) 1150, a variable DGD (VDGD) element 1160 to produce a variable DGD, a DOP monitor 1170 for measuring the degree of polarization of the light, and a PMD control circuit within the control unit 1190. The polarization controller 1150 may use various implementations, including the fiber-squeezer controllers disclosed in the incorporated U.S. Pat. No. 6,493,474. The DOP monitor 1170 may be configured to tap a portion of the signal for the monitoring operation and send the remaining signal to the channel receiver 1180. As illustrated, the PMD control circuit controls both the polarization controller 1150 and the variable DGD element 1160 in response to the measured DOP from the monitor 1170. Hence, the control is a feedback control and operates dynamically to produce real-time PMD compensation. In implementations, a microprocessor may be used in the control unit 1190 to perform the computations for the DGD measurement and the PMD compensation.

Figure 13:
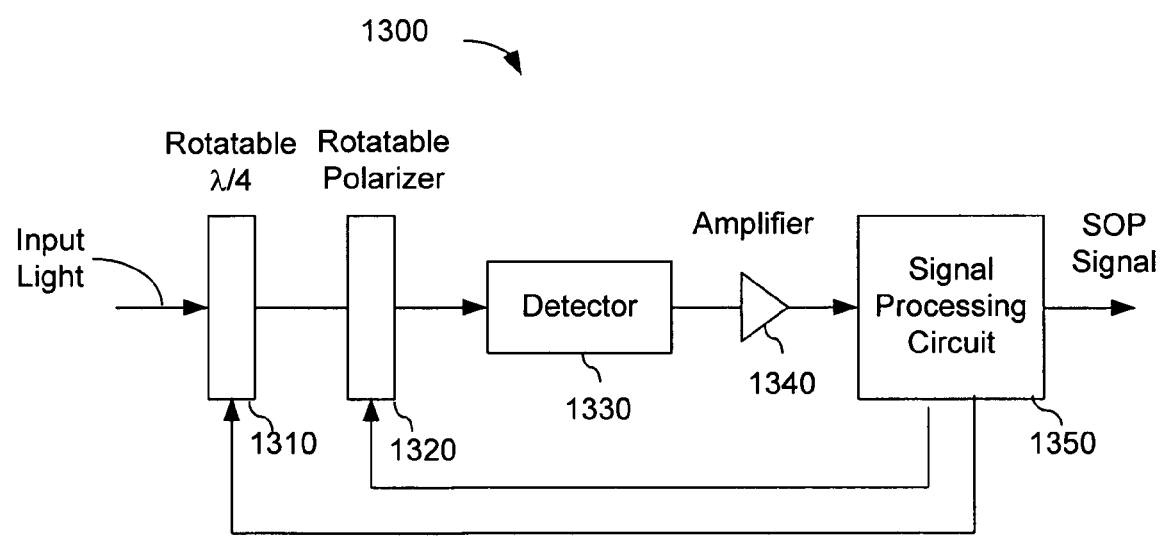
FIGS. 13, 14, and 15 show three examples of optical monitoring devices that use a rotatable quarter waveplate and a rotatable polarizer as a polarization scrambler.

The polarimeter 1140 in FIG. 11 may be implemented in various configurations. FIG. 13 shows one exemplary implementation 1300 by using a rotatable quarter-wave plate 1310 and a rotatable polarizer 1320 to sequentially process input light. The plates 1310 and 1320 are controlled, e.g., by the circuit 1350, to rotate at different rotational speeds or frequencies. In this and other implementations, the rotatable wave plate 1310 may be replaced by a polarization controller such as the fiber-squeezer controller disclosed in the attached U.S. Pat. No. 6,493,474. An optical detector 1330 converts the processed light into a detector signal and a signal processing circuit 1350 further processes the detector signal to measure the SOP of the light. A signal amplifier 1340 may be optionally coupled between the detector 1330 and the circuit 1350 to amplify the signal. Hence, in the configuration in FIG. 11, as the filter 1130 scans through different channels, the polarimeter 1300 measures the SOP one channel at a time. Alternatively, the configuration in FIG. 11 may be modified to place the tunable filter 1130 between the detector 1330 and the polarizer 1320 of the polarimeter 1300.

Figure 14:
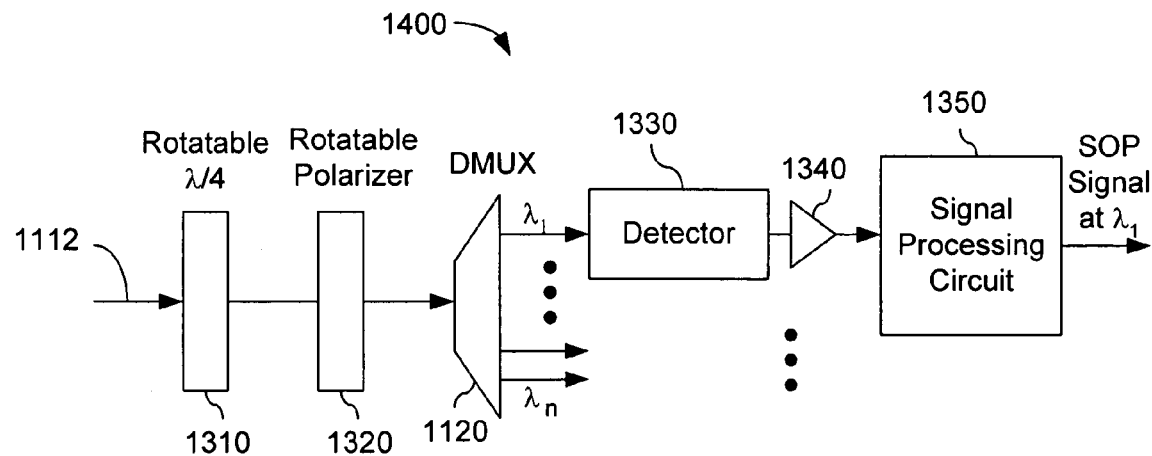
Figure 15:
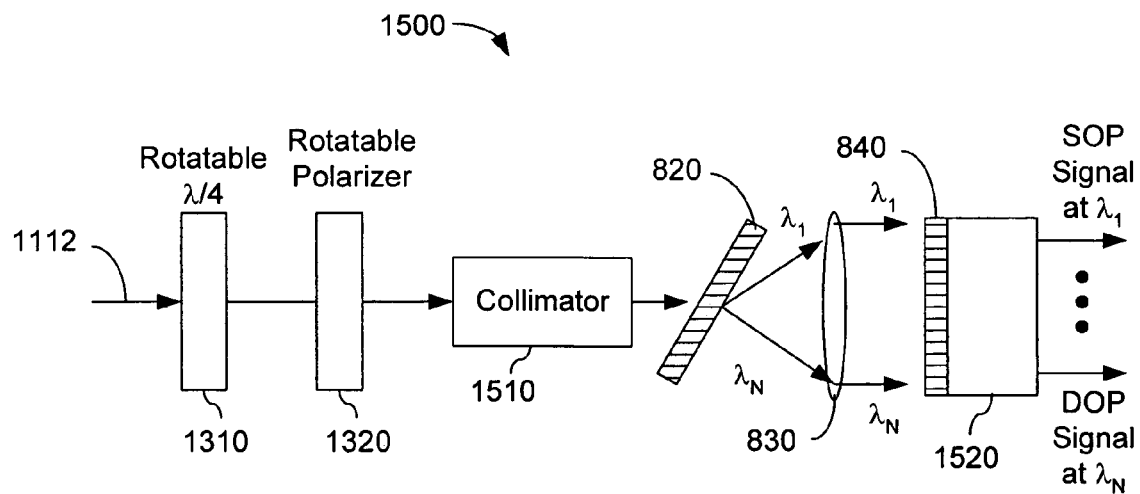

A polarimeter may also be configured to measure SOP of multiple channels in parallel at the same time. FIGS. 14 and 15 show two examples. In FIG. 14, the polarimeter 1400 uses a demultiplexer 1120 to separate different channels output by the quarter-wave plate 1310 and the polarizer 1320. For each channel, a designated optical detector 1330 and a designated signal processing circuit 1350 are used to process the channel signal to determine the SOP of that channel. Hence, all channels are monitored in parallel with one another at the same time.

FIG. 15 shows a different design 1500 where a diffraction grating 820 and a collimating lens 830 are used to spatially separate the different channels in a manner similar to the design in FIG. 8 for a different application. A processing circuit 1520 is used to process the detector outputs to produce the SOP signals for different channels.

In absence of PMD in an input optical signal, the SNR of the signal can be directly determined from the DOP measurement. Assume $P_s$ is the power of the signal which is polarized and $P_n$ is the power of the noise which is unpolarized. The DOP can be computed by the following equation:

$$DOP = \frac{P_s}{P_s + P_n} = \frac{P_s/P_n}{1 + P_s/P_n}.$$

Accordingly, the SNR can be computed from DOP:

$$SNR = \frac{P_s}{P_n} = \frac{DOP}{1 - DOP}.$$

Here, the DOP can be computed from the maximum and minimum power levels from the measurements. When DOP is 1, the SNR is infinite and when DOP is zero, the SNR is zero.

Figure 16:
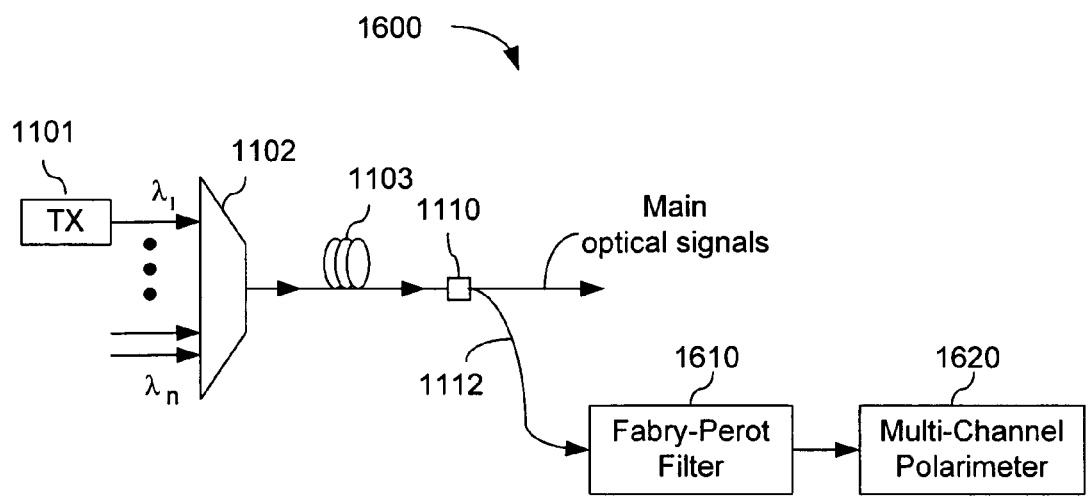
FIG. 16 shows a fiber system that uses a Fabry-Perot filter and sequential or parallel multi-channel polarimeters to monitor the SOP of each channel.
Figure 17:
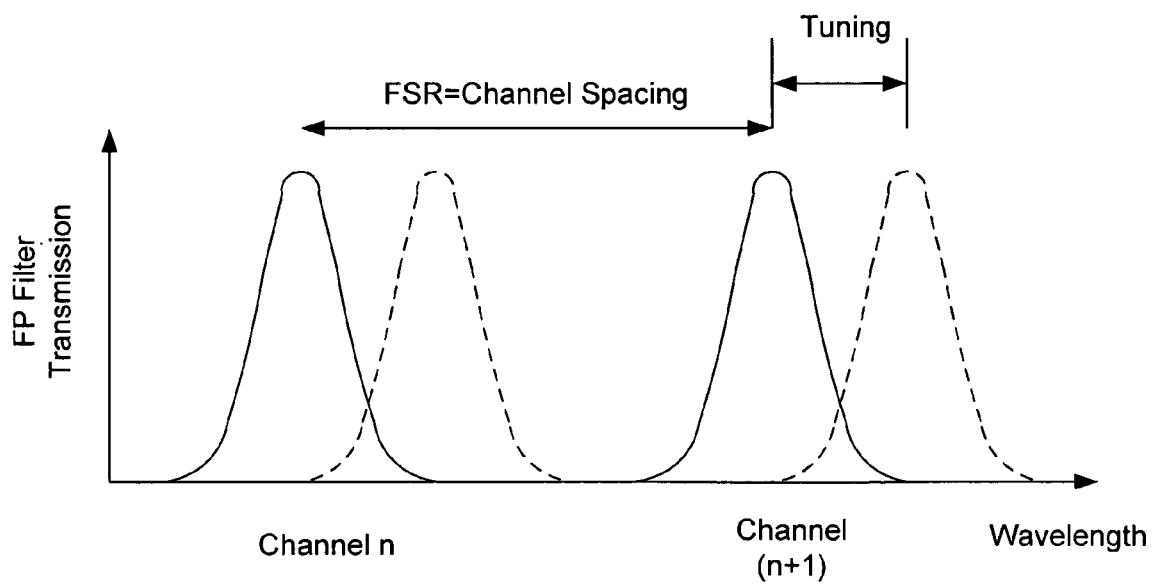
FIG. 17 illustrates operations of the Fabry-Perot filter in FIG. 16.

FIG. 16 shows a fiber system 1600 that uses any one of the above sequential or parallel multi-channel polarimeters to monitor the SOP of each channel. A fiber coupler 1110 is used to split a fraction of the input light with multiple channels to produce a monitor beam 1112. A tunable Fabry-Perot filter 1610 is used to filter the monitor beam 1112 to transmit all WDM channels at the same time to a multi-channel polarimeter 1620. This may be accomplished by designing the Fabry-Perot filter 1610 to have a free spectral range (FSR) equal to the channel spacing of the WDM channels or a multiplicity of the channel spacing. In operation, the tunable Fabry-Perot filter 1610 is tuned to measure the DGD as illustrated in FIG. 12. FIG. 17 further shows the spectrum of the filter 1610 where a tuning in the filter 1610 causes the same amount of frequency shift in the transmission of all channels. The polarimeter 1620 may be a sequential multi-channel polarimeter having a tunable filter or a parallel multi-channel polarimeter as shown in FIGS. 14 and 15.

In some WDM systems, the channel spacing may be 50 GHz, 100 GHz, or 200 GHz. Assuming the finesse of the filter 1610 is 100, the resolution bandwidth of the filter is 1 GHz and should be sufficient to resolve the spectrum of a 10 Gb/s signal. As described above, the DGD of each channel can be calculated based on the measured SOP in each channel as illustrated in FIG. 12.

Figure 18A:
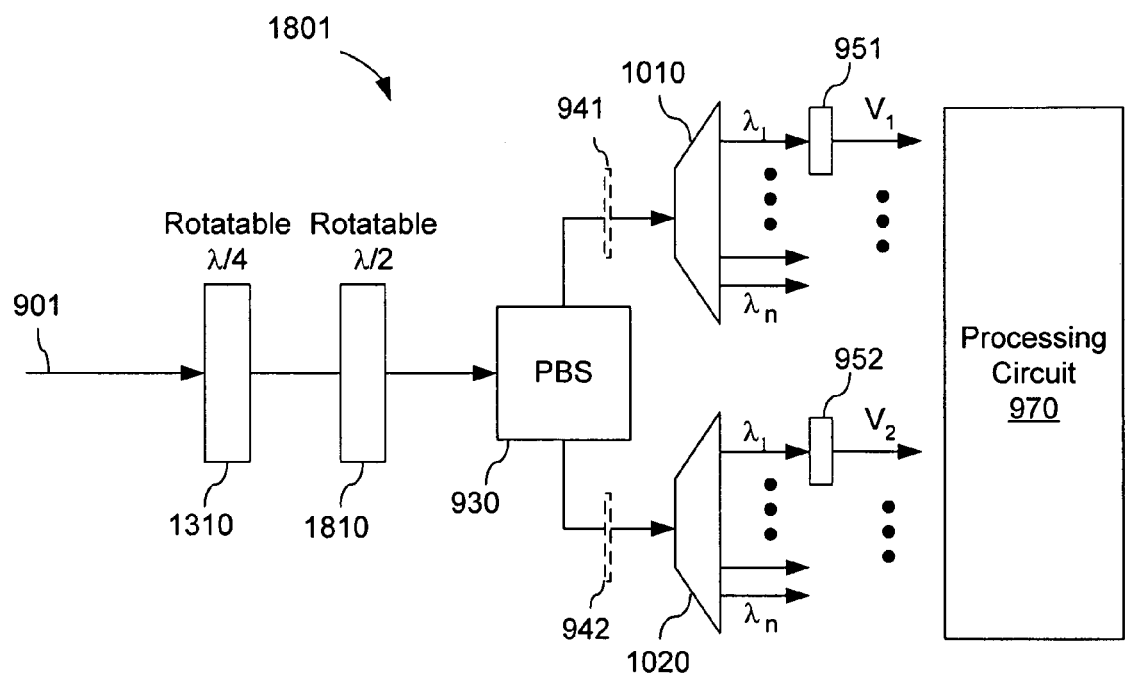
FIGS. 18A and 18B show two examples of WDM optical monitoring devices that use a rotatable quarter waveplate and a rotatable half waveplate as part of the device.
Figure 18B:
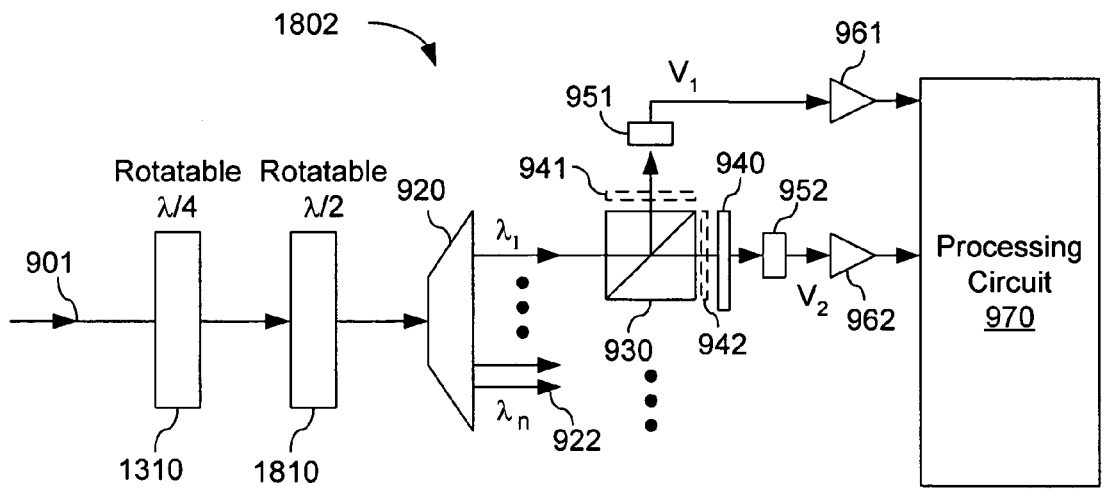
Figure 19A:
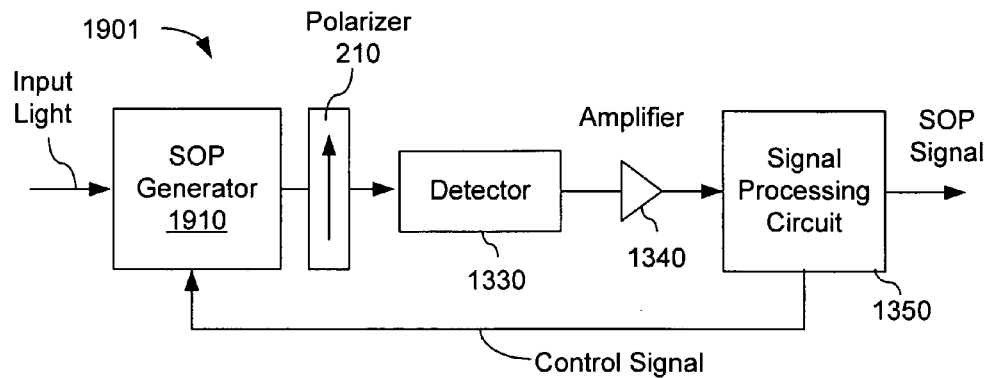
FIGS. 19A, 19B, 19C, 19D, and 19E illustrate examples of optical monitoring devices that use a SOP generator and a fixed optical polarizer.
Figure 19B:
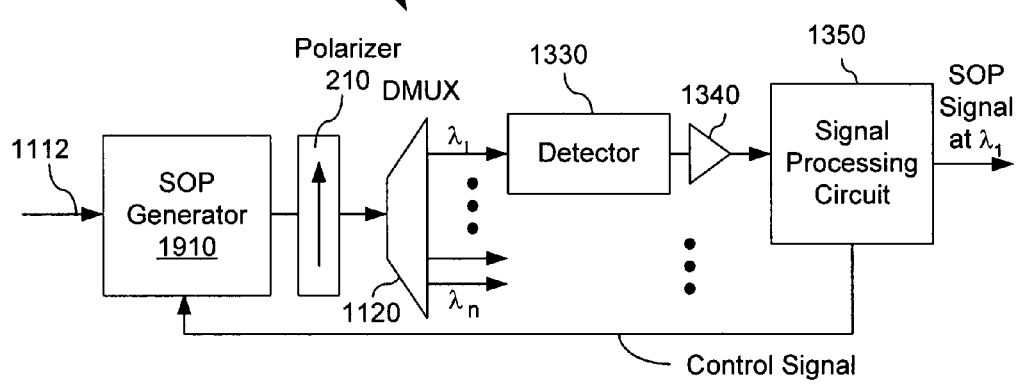
Figure 19C:
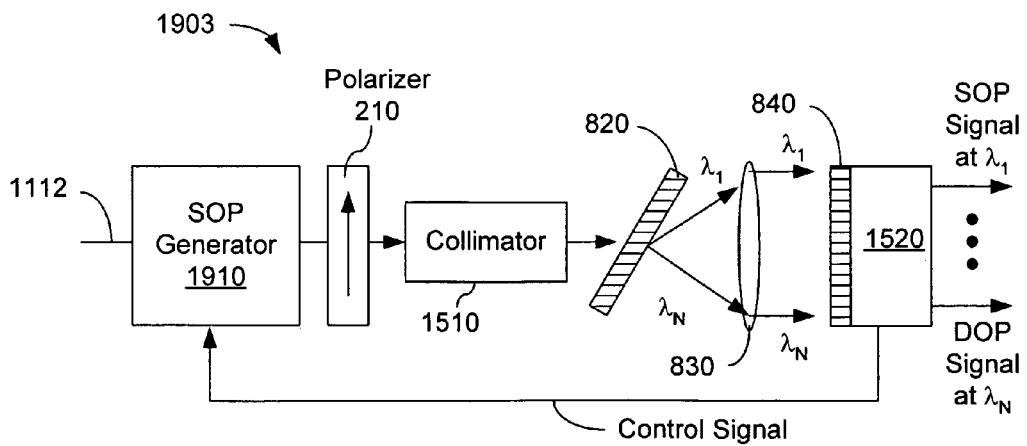
Figure 19D:
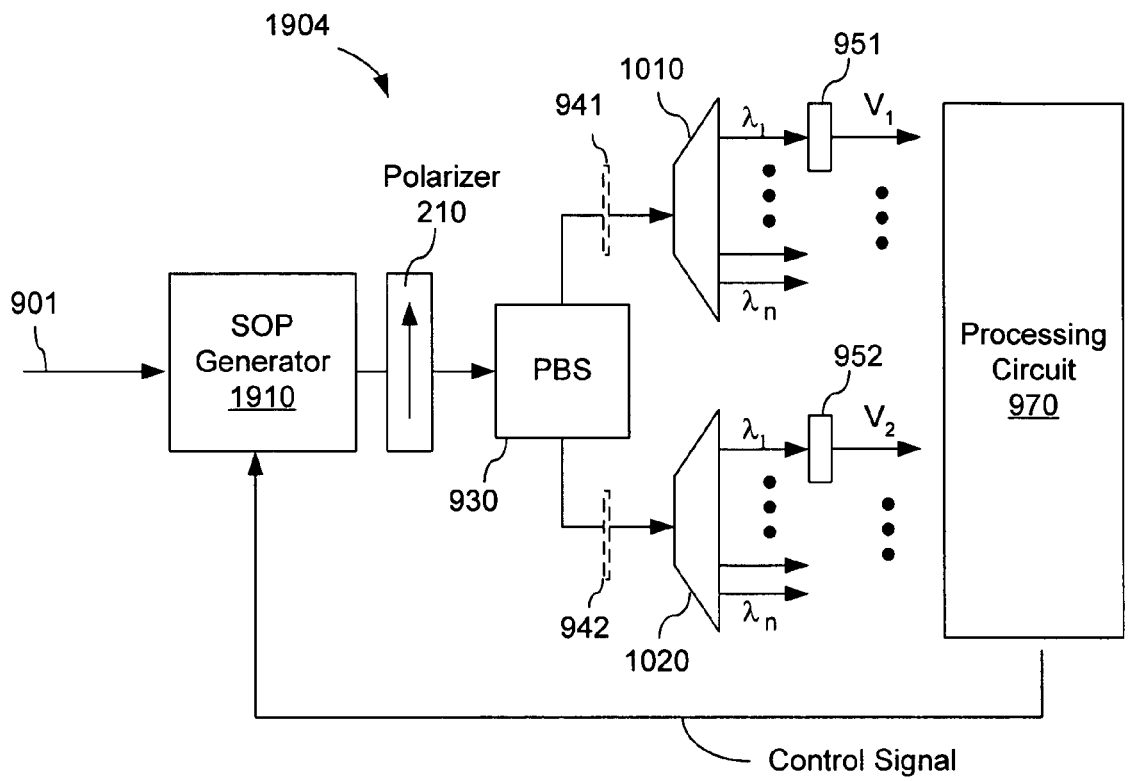
Figure 19E:
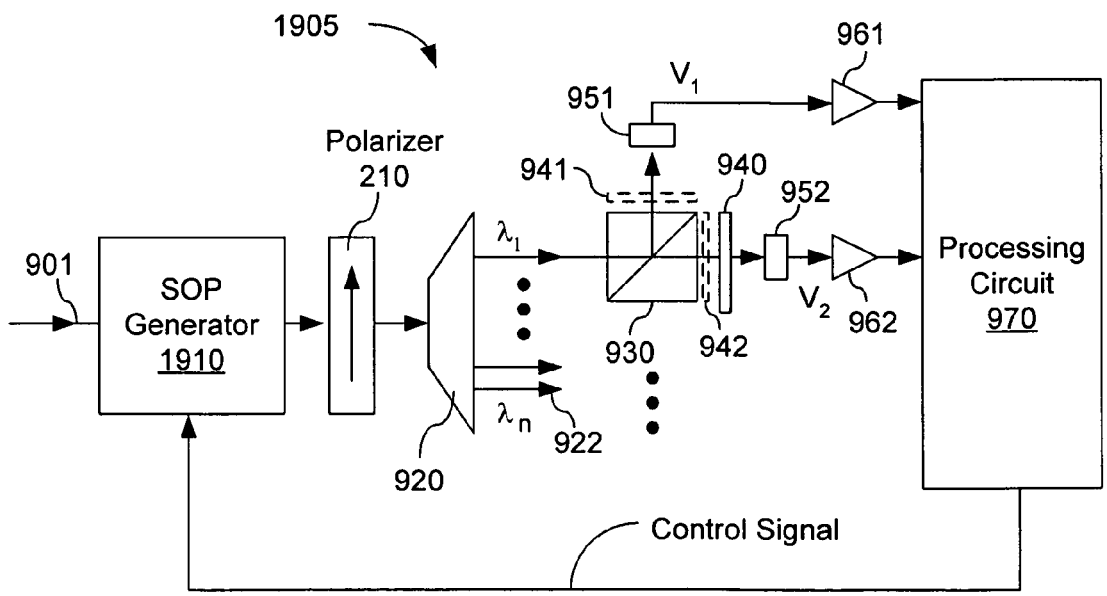

FIGS. 18A and 18B show two exemplary implementations 1801 and 1802 for providing independent monitoring of the signal to noise ratio (SNR) and DGD in WDM systems. In both systems, the input light is sequentially processed by a rotatable quarter-wave plate 1310 and a rotatable half-wave plate 1810. The waveplates 1310 and 1810 rotate at different rotation speeds. Also in both systems, each channel is split into two beams with orthogonal polarizations to have different power levels. In the system 1801, this is achieved by using two different demultiplexers 1010 and 1020 with different channel bandwidth. In the system 1802, a filter 940 is inserted in one of the two output beams to produce the difference. The processing techniques in connection with FIGS. 9 and 10 are applicable here.

In the above described examples shown in FIGS. 13, 14, 15, 18A and 18B, the polarization scrambler formed by the rotatable waveplate 1310 and the rotatable polarizer 1320 may be replaced by a SOP generator and a downstream fixed optical polarizer. The SOP generator may be used to manipulate the polarization of received light to produce any desired SOP among a set of predetermined SOPs on the Poincare sphere.

FIGS. 19A, 19B, 19C, 19D, and 19E illustrate examples 1901, 1902, 1903, 1904, and 1905 of optical monitoring devices that use a SOP generator 1910 and a fixed optical polarizer 1920. The SOP generator 1910 may be configured to be adjustable to produce various SOPs. An external control signal may be used to control the SOP generator 1910 in producing SOPs. In actual implementation, the control signal includes individual control signals for different rotators in the SOP generator 1910.

Figure 20:
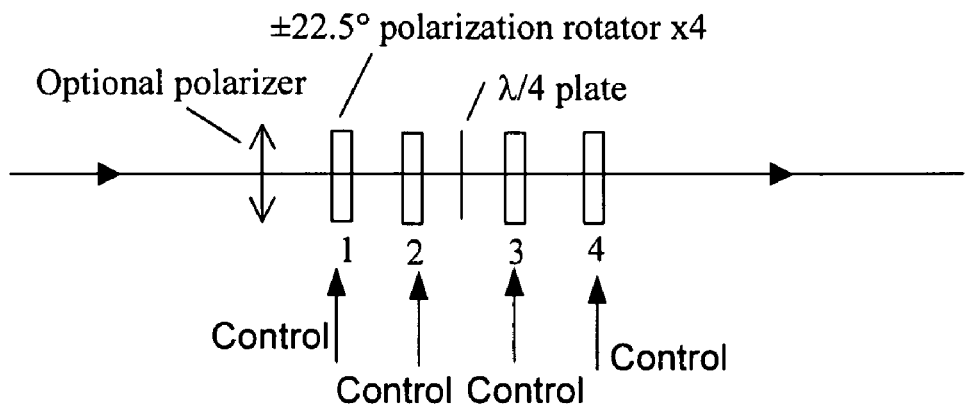
FIGS. 20 and 21 show exemplary implementations of a SOP generator.

FIG. 20 shows one example of a SOP generator. In this example, the SOP generator includes four controllable polarization rotators 1, 2, 3, and 4 that are sequentially placed in the optical path. A quarter waveplate is placed between the rotators 2 and 3 to separate the 4 rotators in to two pairs: rotators 1 and 2 as one pair and rotators 3 and 4 as another pair. In addition, an optional input polarizer may be placed in front of the first rotator 1 for aligning the input polarization with respect to the optical axis (c-axis) of the λ/4 plate. The input polarizer may be oriented in various directions, e.g., aligned with the c-axis, or 45° from the c-axis, or other predetermined angle. Each of the polarization rotators in FIG. 20 may be individually controlled by a control signal as illustrated. Polarization rotations of the rotators are controlled to produce the desired SOPs at the output.

Notably, the SOP generator in FIG. 20 is specifically designed to generate at least 4 and generally more than 4 distinctively different polarization states from an input light beam with a linear input polarization. This feature of the SOP generator in FIG. 20 is significant because any state of polarization of light can be represented by a set of 4 Stockes parameters for polarization. Therefore, when at least 4 measurements can be obtained from an optical sample, an optical device, or an optical module with at least 4 different states of polarization in the probe light, a set of 4 linear equations can be solved to determine the values of the set of 4 Stockes parameters and thus to determine the polarization property of the sample, device or module under test.

In addition, the SOP generator in FIG. 20 may also be used as a SOP analyzer or polarimeter to determine the SOP of received light in any SOP by obtaining at least 4 different measurements of the input light and solve for the set of 4 Stockes parameters of the SOP of the input light.

It is well known that a Poincare sphere can be used to represent any and all states of polarization. Each point on this Poincare sphere has a unique set of coordinates defined by the sphere's three-dimensional axes $S_1$, $S_2$ and $S_3$. A Stokes vector is a 4×1 real matrix of 4 associated Stokes parameters ($S_0$, $S_1$, $S_2$, $S_3$) that completely describes the SOP of the light. As an example, points on the equator of the Poincare sphere represent linear polarization states, the poles represent right-hand and left-hand circular polarization, and other points on the Poincare sphere represent elliptical polarization states.

Mathematically speaking, a minimum of 4 distinctively polarization measurements can be used to completely determine the Stockes parameters. In principle, these 4 distinctively polarization measurements may be obtained in any suitable manner in a particular application. As an example, the 4 Stockes parameters of a beam with a unknown SOP may be determined based upon measured power levels in the following measurements: 1) a polarizer at 0° (e.g., along the horizontal direction) is inserted in the input light and the optical power after the polarizer is measured; 2) Next, the polarizer is rotated by 45° and the corresponding optical power after the polarizer is measured; 3) the polarizer is then rotated by 90 degrees (or –45°) and the optical power after the polarizer is measured; and 4) finally, a right-hand-circular (RHC) or left-hand-circular (LHC) polarizer is inserted into the input light and the optical power after the RHC or LHC polarizer is measured.

The above power measurements can then be used to determine the Stockes parameters of the input SOP as follows. $S_0$ is the average power of the entire light beam (I); $S_1$ is the difference in power between the horizontal (0 degree) and vertical (90 degrees) linear polarization components of the beam ($I_0-I_{90}$); $S_2$ indicates the power difference between the +45-degree and –45-degree linear polarizations, ($I_{45}-I_{-45}$); and $S_3$ is the power difference between the right hand circular (RCP) and left-hand circular (LCP) polarizations: ($I_{RCP}-I_{LCP}$). The Stokes vector has a magnitude equal to $(S_1^2+S_2^2+S_3^2)^{1/2}$ and originates from the center of the Poincare sphere. The three Stokes parameters can be normalized by the relative optical power values ($s_1=S_1/S_0$, $s_2=S_2/S_0$, $s_3=S_3/S_0$)

In one implementation of the SOP generator in FIG. 20, each polarization rotator may be a magneto-optic (MO) rotator to avoid any mechanical moving part in the SOP generator. This use of MO rotators or other polarization rotators without moving parts can improve the reliability and operating life of the device.

A polarization rotator, such as a MO rotator, suitable for the SOP generator in FIG. 20 may be designed to have the following properties: (1) when a positive voltage above the saturation voltage Vsat of the MO rotator is applied to the MO rotator (i.e., $V \geq +Vsat$), the MR rotator rotates the SOP of light by +22.5°; (2) when a negative voltage above the saturation voltage Vsat is applied (i.e., $V \leq -Vsat$), the rotator rotates the SOP by –22.5°; (3) when rotators 1 and 2 (or 3 and 4) are rotated in the same direction, the net rotation of the pair of rotators 1 and 2 or rotators 3 and 4 is 45°; and (4) when rotators 1 and 2 (or 3 and 4) are rotated in the opposite directions, the net rotation of the pair is 0°. Alternatively, other types of polarization rotators such as liquid crystal polarization rotators and solid-state birefringent crystal polarization rotators may also be configured with the above operating states with appropriate control signals.

Accordingly, this particular SOP generator can be used to generate at least the following 5 distinctly different states of polarization when the input SOP is linear and is aligned with the c-axis of the λ/4 plate:

(1) A linear SOP at 0° is generated when rotators 1 and 2 are rotated at opposite directions and rotators 3 and 4 are rotated at opposite directions;

(2) A linear SOP at +45° is generated when rotators 1 and 2 are rotated at opposite directions, but rotators 3 and 4 are each rotated by +22.5°;

(3) A linear SOP at –45° is generated when rotators 1 and 2 are rotated at opposite directions, but rotators 3 and 4 are each rotated by –22.5°;

(4) A right-hand circular (RHC) polarization state is generated when rotators 1 and 2 are each rotated by +22.5°; and (5) A left-hand circular (LHC) polarization state is generated when rotators 1 and 2 are each rotated by –22.5°.

TABLES 1 and 2 are logic tables with SOPs of different settings of the rotators 1, 2, 3, and 4 for two configurations of the SOP generator in FIG. 20. The first row in each table shows both the direction and rotation in each of the four rotators and the remaining rows show only the directions of the rotations by the rotators and the amount of rotation is fixed at 22.5 degrees. The SOP generator in the 45-degree configuration in TABLE 2 has 6 distinctively different polarization states. The SOP in both configurations has degenerate states where two sets of different settings of the rotators generate the same state of polarization at the output. For example, the top four different settings for the 4 rotators all generate the same 0-degree linear polarization at the output.

TABLE 1

SOPs when Input SOP is aligned with quarter wave plate

| Rotator 1 | Rotator 2 | Rotator 3 | Rotator 4 | SOP |
|---|---|---|---|---|
| +22.5° | –22.5° | +22.5° | –22.5° | 0° linear |
| + | – | – | + | 0° linear |
| – | + | + | – | 0° linear |
| – | + | – | + | 0° linear |
| + | – | + | + | 45° linear |
| – | + | + | + | 45° linear |
| + | – | – | – | –45° linear |
| – | + | – | – | –45° linear |
| + | + | + | + | RHC |
| + | + | – | + | RHC |

TABLE 1-continued

SOPs when Input SOP is aligned with quarter wave plate

| Rotator 1 | Rotator 2 | Rotator 3 | Rotator 4 | SOP |
|---|---|---|---|---|
| + | + | + | − | RHC |
| + | + | − | − | RHC |
| − | − | + | + | LHC |
| − | − | − | + | LHC |
| − | − | + | − | LHC |
| − | − | − | − | LHC |

TABLE 2

SOPS when Input SOP is aligned 45° from
c-axis of the quarter wave plate

| Rotator 1 | Rotator 2 | Rotator 3 | Rotator 4 | SOP |
|---|---|---|---|---|
| +22.5° | −22.5° | +22.5° | −22.5° | RHC |
| + | − | − | + | RHC |
| − | + | + | − | RHC |
| − | + | − | + | RHC |
| + | − | + | + | RHC |
| − | + | + | + | RHC |
| + | − | − | − | RHC |
| − | + | − | − | RHC |
| + | + | + | + | 90° linear |
| + | + | − | + | 45° linear |
| + | + | + | − | 45° linear |
| + | + | − | − | 0° linear |
| − | − | + | + | 0° linear |
| − | − | − | + | −45° linear |
| − | − | + | − | −45° linear |
| − | − | − | − | −90° linear |

Figure 21:
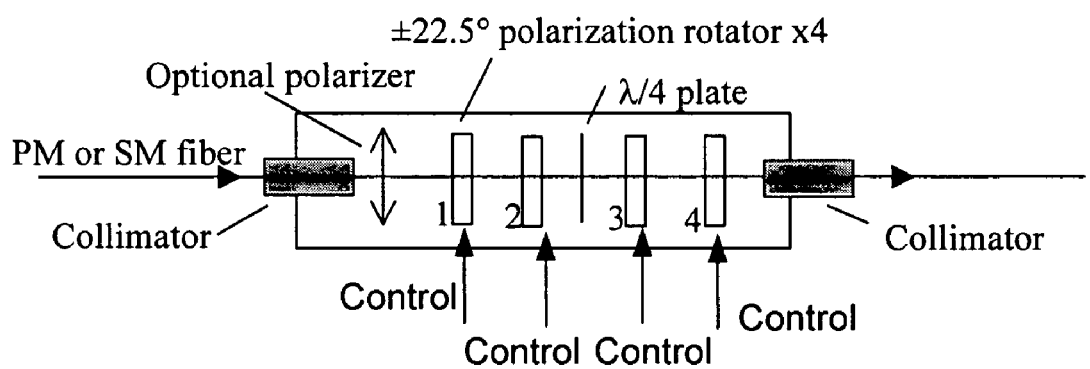

FIG. 21 shows an example of a packaged SOP generator based on the design in FIG. 20 where the generator is packaged or pigtailed with polarization-maintaining (PM) or single mode (SM) fibers. As illustrated, a housing may be used to hold the rotators and the waveplate along with the optional input polarizer. Two fiber collimators may be used at the input and output ports of the SOP generator and may be engaged to the input and output PM or SM fibers. The fibers may also be single mode PM fibers.

In operating the SOP generator in FIG. 20 or FIG. 21 to generate different output SOPs, the SOP of an input light signal with a linear polarization is first determined and then the relative orientation between the input SOP and the quarter wave plate is set at a predetermined angle, e.g., at the zero degree as in the configuration in TABLE 1 or at 45 degrees as in TABLE 2.

Figure 22:
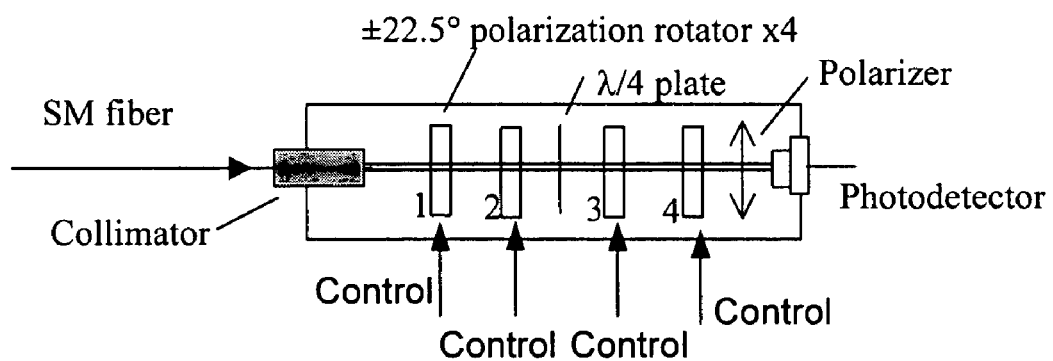
FIG. 22 shows a device that uses a SOP generator to measure the degree of polarization of light.

When the SOP generator in FIG. 20 or FIG. 21 is used as an SOP analyzer to measure SOP and DOP of light, an input beam with an unknown SOP is sent into the SOP generator from the right port (the rotator 4) in FIG. 20 and an optical detector at the left port (rotator 1) to receive the light transmitting through the SOP generator. FIG. 22 shows one exemplary setup for using the SOP generator as a SOP analyzer or polarimeter. An output polarizer with a fixed linear polarization is placed between the output of the SOP generator and the optical detector to filter the output light from the SOP generator so the received light at the optical detector is polarized by the fixed polarizer. The power of the output from the output polarizer is measured and used to determine the SOP of the input light.

In this operation, the SOP generator may be used to generate the minimum 4 different polarization states for the polarizer to analyze by rotating the SOP of the input light. Hence, the 4 rotators in the SOP generator used for analyzing unknown SOP of the input light in FIG. 22 are controlled to rotate the SOP to generate 4 different output states for the measurement. For the previous example for doing 4 different polarization measurements by rotating a polarizer and using a RHC or LHC polarizer in order to determine the 4 Stockes parameters, the SOP generator in FIG. 22 may be used to rotate the SOP of the input light instead to achieve the 4 equivalent power measurements: 1) the 4 rotators are controlled so the input SOP is not changed and is directly sent to the polarizer in front of the optical detector and the optical power after the polarizer is measured; 2) the 4 rotators are controlled to rotate the SOP by 45° and the optical power after the polarizer is measured again; 3) the 4 rotators are controlled to rotate the input SOP by 90 or −45° and the optical power after the polarizer is measured for the third time; and 4) the 4 rotators are controlled to convert the input SOP into RHC (or LHC) and measure the optical power after the polarizer. The above steps are used here to illustrate the mechanism that the SOP generator in FIG. 22 is used to convert the input SOP into 4 different SOPs in order to get 4 different power measurements. In actual operation of the SOP generator in FIG. 22, 4 or more different settings for generating different output SOPs are used to obtain different measurements. For example, if the direction of the polarizer in front of the optical detector in FIG. 22 is aligned with the optic axis of the λ/4 plate in the SOP generator, the 4 rotators may be set to 4 different combinations in TABLE 1 that produce different output SOPs in TABLE 1 to obtain the 4 measurements. When the direction of the polarizer in front of the optical detector in FIG. 22 is aligned at 45 degrees with respect to the optic axis of the λ/4 plate in the SOP generator, the 4 rotators may be set to 4 different combinations in TABLE 2 that produce different output SOPs in TABLE 2 to obtain the 4 measurements.

Figure 23:
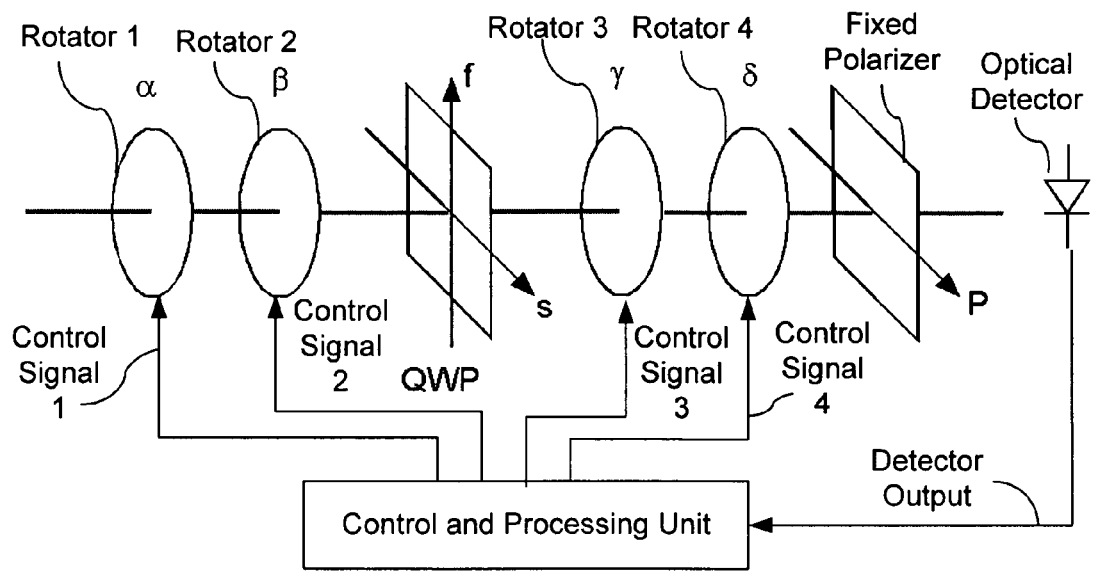
FIG. 23 shows an example of a 4-rotator polarimeter with a control and processing unit.

FIG. 23 further shows a polarimeter based on the design in FIG. 22 where the polarizer in front of the optical detector is aligned to be parallel to the slow axis of the λ/4 plate. Assume the 4 polarization rotators 1, 2, 3, and 4 operate with polarization rotation angles of $\alpha$, $\beta$, $\gamma$, and $\oplus$, respectively and there is no optical loss in the transmission through the polarimeter, the Mueller matrix of the polarimeter can be expressed by the following 4×4 matrix M(T):

$$M(T) = \begin{pmatrix} 1 & \cos2(\alpha+\beta)\cos2(\gamma+\delta) & \sin2(\alpha+\beta)\cos2(\gamma+\delta) & \sin2(\gamma+\delta) \\ 1 & \cos2(\alpha+\beta)\cos2(\gamma+\delta) & \sin2(\alpha+\beta)\cos2(\gamma+\delta) & \sin2(\gamma+\delta) \\ 0 & 0 & 0 & 0 \\ 0 & 0 & 0 & 0 \end{pmatrix},$$

When the Stokes vector $S=(S_0, S_1, S_2, S_3)$ represents the input polarization state, then the output optical power ($S_0'$) is $$S_0' = \frac{1}{2}[S_0 + \cos2(\alpha+\beta)\cos2(\gamma+\delta)S_1 + \sin2(\alpha+\beta)\cos2(\gamma+\delta)S_2 + \sin2(\gamma+\delta)S_3].$$

In the expression for the output optical power of the polarimeter, the 4 different rotation angles for the rotators appear in pairs where the rotation angles for the rotators 1 and 2 on one side of the λ/4 plate appear as a sum of ($\alpha+\beta$) and the rotation angles for the for the rotators 3 and 5 on the other side of the λ/4 plate appear as a sum of ($\gamma+\delta$). Hence, two double stage rotation angles θ and Φ can be defined to represent the two sums, respectively:

$$\theta = \alpha + \beta, \text{ and}$$

$$\Phi = \gamma + \delta.$$

In the exemplary design shown in FIGS. 20–22, the rotators, such as magnetooptic crystals, are assumed to have the following binary steady-state values $$\alpha = \beta = \gamma = \delta = \pm 22.5°.$$

Under this condition, the possible combinations for the double stage rotation angles become $$\begin{pmatrix} \theta \\ \varphi \end{pmatrix} = \begin{cases} 45° \\ 0° \\ -45° \end{cases}.$$

Therefore, the optical output $S_0'$, the double stage rotation angles θ and Φ, and the binary values for the rotation angles of the 4 rotators can be used to show that there are total 5 different output power values for all possible combinations of θ and Φ. Any 4 of such combinations yield enough information for the calculation of the input SOP.

More specifically, the optical output $S_0'$ can be expressed as a function of the angles of θ and Φ:

$$S_0'(\theta, \varphi) = \frac{1}{2}[S_0 + S_1 \cos 2\theta \cos 2\varphi + S_2 \sin 2\theta \cos 2\varphi + S_3 \sin 2\varphi],$$

Accordingly, the following output states for the output $S_0'$ can be obtained by controlling the rotators:

$$S_0'(0°, 0°) = \frac{1}{2}(S_0 + S_1),$$

$$S_0'(\pm 45°, 0°) = \frac{1}{2}(S_0 \pm S_2), \text{ and,}$$

$$S_0'(\theta, \pm 45°) = \frac{1}{2}(S_0 \pm S_3).$$

Therefore, the Stockes parameters for the unknown SOP of the input light to the polarimeter can be determined as follows:

$$S_0 = S_0'(\theta, 45°) + S_0'(\theta, -45°) = S_0'(45°, 0°) + S_0'(-45°, 0°),$$

$$S_1 = 2S_0' - S_0'(45°, 0°) - S_0'(-45°, 0°)$$

$$S_2 = S_0'(45°, 0°) - S_0'(-45°, 0°),$$

$$S_3 = S_0'(\theta, 45°) - S_0'(\theta, -45°).$$

In an actual implementation of the polarimeter, a control and processing unit may be used to generate control signals 1, 2, 3, and 4 to control the rotators 1, 2, 3, and 4, respectively, and to process the detector outputs from the optical detector that correspond to different combination of rotator settings for the rotators. A microprocessor or computer may be included in the control and processing unit and is programmed to perform certain control and data processing operations. The Muller matrix equation is then solved based on the detector outputs to determine the SOP of the receive light. The DOP of the input light can then be determined from the SOP. The signal to noise ratio (SNR) of the input signal can also be determined based on the relation of SNR=(DOP)/(1−DOP).

Figure 24:
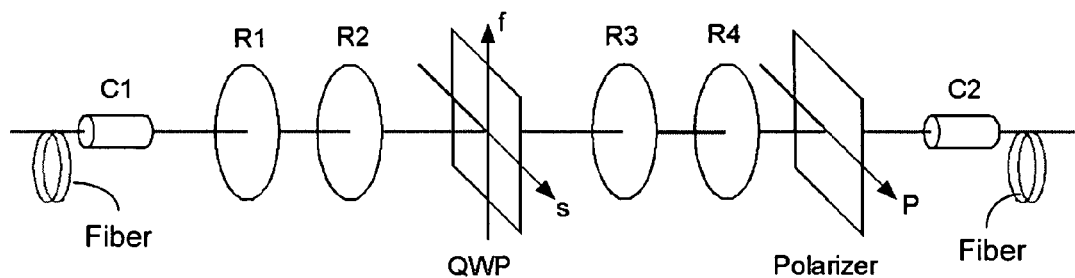
FIGS. 24 and 25 show examples of 4-rotator and 6-rotator polarimeters using optical fibers.

FIG. 24 shows an exemplary fiber implementation of the polarimeter in FIG. 23 where an input fiber is used to deliver the input light and an output fiber is used to receive the output light. Fiber optical collimators C1 and C2 are respectively coupled to the input to the polarimeter and the output, respectively.

In the above SOP generators and SOP-based polarimeters, 4 polarization rotators are used to form two pairs of rotators. To further increase different SOPs of such SOP generators and polarimeters, additional pairs of rotators may be added. The quarter wave plate (QWP) may be placed between any two pairs of rotators.

Figure 25:
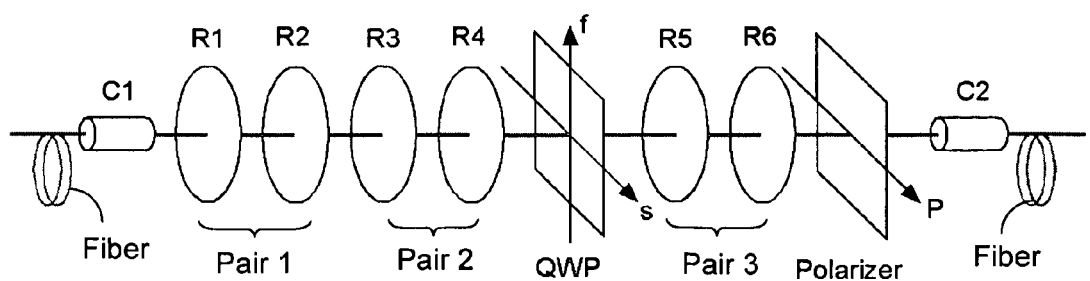

FIG. 25 shows one example of a polarimeter with a total of 6 polarization rotators R1, R2, R3, R4, R5, and R6 to form three pairs of rotators (R1, R2), (R3, R4), and (R5, R6). The quarter wave plate is shown to be between the pairs (R3, R4) and (R5, R6). Alternatively, the quarter wave plate may be placed between the pairs (R1, R2) and (R3, R4). Again, assuming each rotator is configured to operate at two binary polarization rotation angles of ±22.5°, the SOP generator with the three pairs of rotators in this polarimeter can produce 6 distinctly different SOPs when the input is a linear polarization.

TABLE 3 is a logic table for the output SOPs of the SOP generator with the three pairs of rotators in the polarimeter in FIG. 25 when the input light has a linear polarization that is aligned with the slow axis of the quarter wave plate. The 6 distinctly different SOPs are 4 different linear polarization states at 0, +45, −45, and +/−90 degrees, and 2 circularly polarized states in RHC and LHC.

TABLE 3

| Logic table for 6-state polarization generator (0, +45, −45, +/−90, RHC, and LHC) | | | | | | |
|---|---|---|---|---|---|---|
| Rotator 1 | Rotator 2 | Rotator 3 | Rotator 4 | Rotator 5 | Rotator 6 | Output SOP |
| +22.5 | −22.5 | +22.5 | −22.5 | +22.5 | −22.5 | 0 |
| + | − | + | + | − | − | 0 |
| + | − | + | − | − | + | 0 |
| + | − | − | − | + | + | 0 |
| + | − | − | + | − | + | 0 |
| + | − | − | + | + | − | 0 |
| + | − | + | + | + | − | 45 |
| + | − | + | + | − | + | 45 |
| + | − | + | − | + | + | 45 |
| + | − | − | + | + | + | 45 |
| + | − | − | − | + | − | −45 |
| + | − | − | − | − | + | −45 |
| + | − | − | + | − | − | −45 |
| + | − | + | − | − | − | −45 |
| + | − | + | + | + | + | 90 |
| + | − | − | − | − | − | −90 |
| − | + | + | − | + | − | 0 |
| − | + | + | − | − | + | 0 |
| − | + | − | − | + | + | 0 |
| − | + | − | + | − | + | 0 |
| − | + | − | + | + | − | 0 |
| − | + | + | + | + | − | 45 |
| − | + | + | + | − | + | 45 |
| − | + | + | − | + | + | 45 |
| − | + | − | + | + | + | 45 |
| − | + | + | − | − | − | −45 |
| − | + | − | − | + | − | −45 |
| − | + | − | + | − | − | −45 |

TABLE 3-continued

Logic table for 6-state polarization generator
(0, +45, −45, +/−90, RHC, and LHC)

| Rotator 1 | Rotator 2 | Rotator 3 | Rotator 4 | Rotator 5 | Rotator 6 | Output SOP |
|---|---|---|---|---|---|---|
| − | + | + | − | − | − | −45 |
| − | + | + | + | + | + | 90 |
| − | + | − | − | − | − | −90 |
| + | + | + | − | + | − | RHC |
| + | + | + | + | − | − | RHC |
| + | + | + | − | − | + | RHC |
| + | + | − | − | + | + | RHC |
| + | + | − | + | − | + | RHC |
| + | + | − | + | + | − | RHC |
| + | + | + | + | + | − | RHC |
| + | + | + | + | − | + | RHC |
| + | + | + | − | + | + | RHC |
| + | + | − | + | + | + | RHC |
| + | + | − | − | + | − | RHC |
| + | + | − | − | − | + | RHC |
| + | + | − | + | − | − | RHC |
| + | + | + | − | − | − | RHC |
| + | + | + | + | + | + | RHC |
| + | + | − | − | − | − | RHC |
| − | − | + | − | + | − | LHC |
| − | − | + | + | − | − | LHC |
| − | − | + | − | − | + | LHC |
| − | − | − | + | − | + | LHC |
| − | − | − | + | + | − | LHC |
| − | − | + | + | − | − | LHC |
| − | − | + | − | − | + | LHC |
| − | − | + | − | + | + | LHC |
| − | − | − | + | + | + | LHC |
| − | − | − | − | + | − | LHC |
| − | − | − | − | − | + | LHC |
| − | − | − | + | − | − | LHC |
| − | − | + | − | − | − | LHC |
| − | − | + | + | + | + | LHC |
| − | − | − | − | − | − | LHC |

Like the SOP generator with 4 rotators, the SOP generator in the polarimeter in FIG. 25 has degenerate SOPs that are produced by different combinations of rotator settings. The rotator settings and the corresponding SOPs may be organized under the 6 different SOPs with respect to different combined rotations of the rotator pairs. Because the rotator pairs (R1, R2) and (R3, R4) are on the same side of the quarter wave plate, the net rotation for the first four rotators R1, R2, R3, and R4 is used as an independent control parameter while the net rotation by the pair (R5 and R6) on the other side of the quarter wave plate is used as another independent control parameter. The combinations of these two net rotation parameters for the 6 distinctly different SOPs are listed in TABLE 4.

TABLE 4

Six Different SOPs of SOP Generator in FIG. 25

| Combined rotation angle of R5 and R6 | Combined rotation angle of R1~R4 | Output SOP | Orientation definition |
|---|---|---|---|
| 0° | 0° | Linear along X | X axis is along polarizer P, Y vertical to P, Z point from C2 to C1 |
| 0° | 45° | Linear along 45° | |
| 0° | −45° | Linear along −45° | |
| 0° | 90° | Linear along Y | |
| 45° | Arbitrary | LCP | |
| −45° | Arbitrary | RCP | |

Similarly, the SOP generator with 4 rotators in the polarimeter in FIG. 24 can be controlled by controlling the net rotations by the two pairs (R1, R2) and (R3, R4) in the listed 5 different combinations to produce the 5 SOPs.

TABLE 5

Five Different SOPs of SOP Generator in FIG. 24

| Combined rotation angle of R3 and R4 | Combined rotation angle of R1 and R2 | Output SOP | Orientation definition |
|---|---|---|---|
| 0° | 0° | Linear along X | X axis is along polarizer P, Y vertical to P, Z point from C2 to C1 |
| 0° | 45° | Linear along 45° | |
| 0° | −45° | Linear along −45° | |
| 45° | Arbitrary | LCP | |
| −45° | Arbitrary | RCP | |

Figure 26:
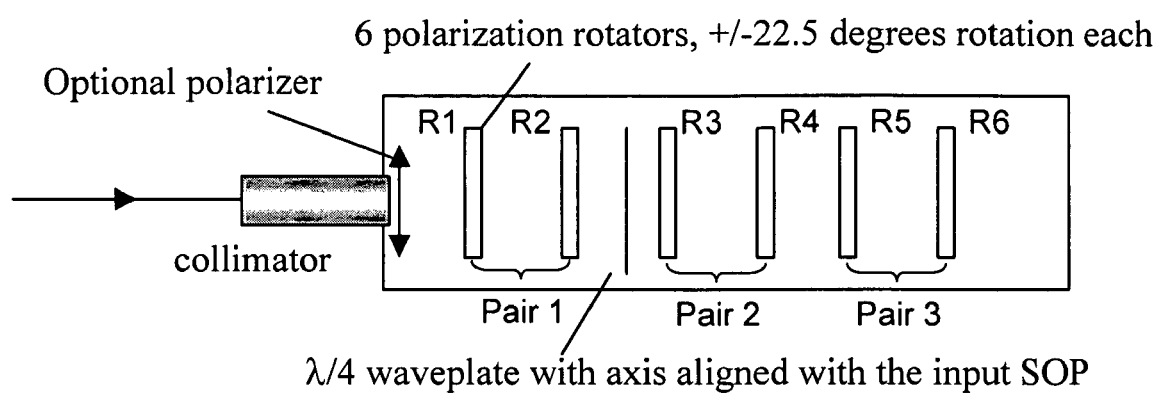
FIG. 26 shows another example of a 6-rotator polarimeter.
Figure 27:
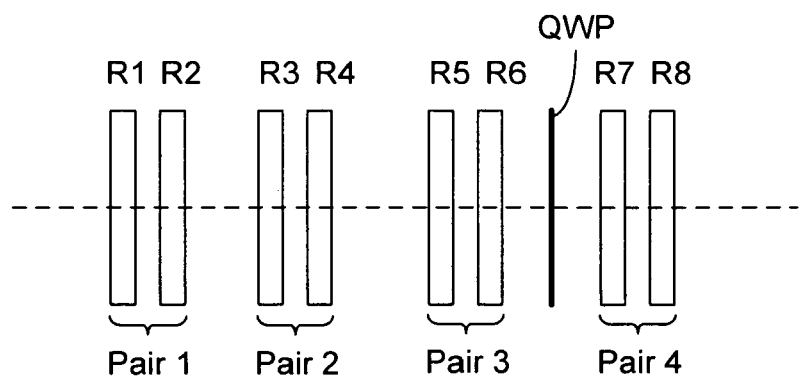
FIG. 27 shows an example of a 8-rotator polarimeter.

FIG. 26 show another 6-rotator SOP generator where the quarter wave plate is placed between the first two pairs (R1, R2) and (R3, R4). FIG. 27 shows an example where 8 polarization rotators are used to form a SOP generator.

In the above examples, the position of the quarter-wave plate is shown to be between different pairs of rotators, e.g., between the third and fourth rotators. This position makes the analysis of the operation of the system intuitive. The quarter-wave plate, however, may be placed in any position in the train of 4 or more rotators, e.g., before the first rotator, after the last rotator, or any position in between. In addition, the number of rotators may be 4, 5, 6, 7, 8 and so on. Furthermore, the above binary rotation angles for each rotator may be set to values other than 22.5 degrees. For example, in order to increase the number of states, smaller angles may be used such as +/−11.125 degrees and other desired values.

The above exemplary 4-, 6-, and 8-rotator SOP generators are used to generate at least four distinctive SOPs for solving the Muller matrix equation for either determining the SOP of input light or measure the polarization property of an optical device or module or an optical birefringent material. The 4-rotator SOP generate is in principle sufficient with its 4 different SOPs. However, more than 4 rotators may be used to generate additional distinctive SOPs to facilitate the measurements when there are additional uncertainties caused by non-ideal settings of various elements. For example, the linear polarizer used in the measurement may not be perfectly aligned with the slow or fast axis of the quarter wave plate but has an angular offset relative to the axis of the quarter wave plate. As another example, the rotators may have angular offsets from the desired angles.

The SOP generators with 4 or more rotators are designed in part to produce different SOPs that are distributed over the Poincare sphere to provide as much coverage of the entire sphere as possible for accurate measurements. Ideally, different SOPs should uniformly distributed over the Poincare sphere. The 4-rotator SOP generator provides 3 three SOPs on the equator of the Poincare sphere and 2 SOPs for the two poles where the 6-rotator SOP generator provides an additional SOP on the equator of the sphere. When more than 4 different SOPs are available, measurements may be performed for different combinations of 4 SOPs and the results from different combinations may be averaged to obtain the final result.

The fiber implementations of the 4-rotator design in FIG. 24 and 6-rotator design in FIG. 25 were tested. The input optical beam can be coupled to either of the C1 and C2 ports. However, each device performs different functionalities when input light beam is coupled to the device from different ports. When the input optical beam is coupled to the C1 port, the polarizer before C2 port allow only the polarization state projected to its passing axis to be transmitted to C2 port. Therefore, the output optical power at the C2 port at different rotation angles is a function of the input polarization state. This feature can be used to construct a polarization analyzer or polarimeter for measuring the SOP of the input light. In the other hand, when the input beam is coupled to the C2 port, and aligned to the transmission axis of the polarizer, the output optical beam at the C1 port maintains a constant output power (depending on device PDL) but the SOP is now a function of the rotation angle of the MO rotators. Due to the binary (saturation) nature of each MO rotator, a number of discrete SOPs can be generated depending on the number of rotators and the rotation angle of each rotator. In the test devices, the rotators are the same and are all set at ±22.5 degrees when magnetic field along ±z axis is applied. The polarizer at C2 port can be also aligned to other angles that will generate a different set of SOP. TABLES 4 and 5 above show the output SOPs at the port C1 when the port C2 is used as the input port. When light enters the port C2 in each device in FIGS. 24 and 25 and propagates through a section of single mode fiber after the port C1, the output SOP will be transformed to SOPs that are different from the SOPs listed in TABLEs 4 and 5 due to the birefringence of the SM fiber. However, the relative angle between different SOPs, that is, the angles between any two distinctive SOPs on Poincare sphere will remain the same.

Figure 28:
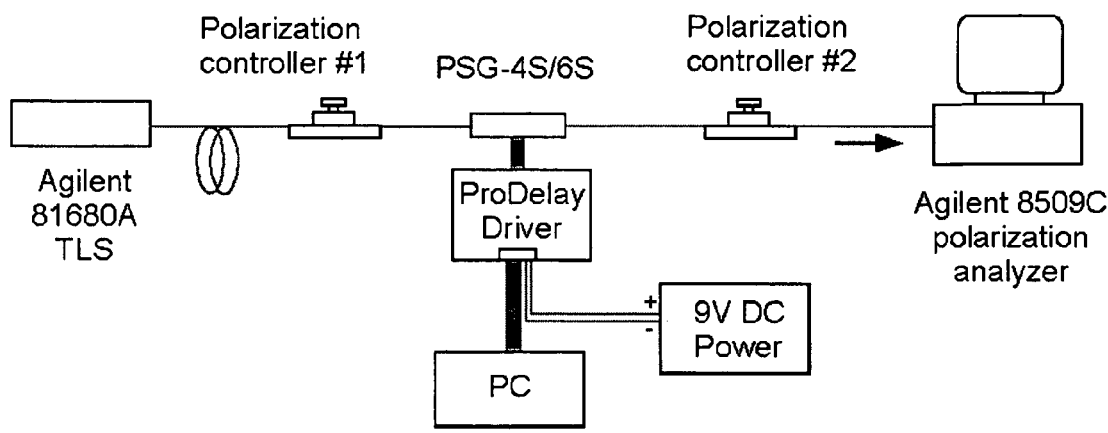
FIG. 28 shows a testing system for testing multi-rotator devices described above.

FIG. 28 shows the testing setup for testing the 4-rotator and 6-rotator devices which are presented by "PSG-4S/6S." The polarization controllers #1 and #2 are placed at the two sides of the device under test. A laser source, e.g., a tunable laser (Agilent 81680 TSL), may be used to generate the input light and the first polarization controller #1 is used to control the polarization of the beam when entering the device under test. The first polarization controller #1 is used to maximize the output optical power that occurs when the input polarization state is aligned to the internal polarizer. The second polarization controller is optional and may be used to move SOP on Poincare sphere for easy display purpose. A polarization analyzer, such as the Agilent 8509C lightwave polarization analyzer, is used to analyze the SOP of the light transmitted through the device under test. A 9-Volt DC power supply is used to supply power to the MO rotators in the device under test. The control unit for the device under test was a driver board designed for the MO rotator driving control. A personal computer (PC) was used as the control and processing unit for the device under test. The 6-rotator device was assembled in an optical head package and mounted on the driver board for this test. The test procedures for 4-rotator and 6-rotator devices are slightly different because the test procedures for the 4-rotator device depend on how the optical head is connected to the driver board. The 6-rotator device were tested as follows.

Prior to the test, the tunable laser source (TLS) was turned on and warmed up (e.g., for 2 hours). Before connecting any cables, the DC power supply is set at 9V and the power supply is turned off. Next, the power cable is connected and wires corresponding to bit 1 through bit 6 for the 6 rotators are connected to a digital I/O card output block. The 6-bit TTL control signals may also be obtained from other means. After the 6-rotator device is connected, the 9V DC power supply is turned on. The default setting is that all LEDs will be on. For best SOP repeatability, it is recommended that 6-rotator device under test can be warmed up for 20 minutes.

A total 6 distinctive SOP states can be generated by a 6-bit digital highs and lows, as shown in the logic table below. The logic high and low of each bit can be directly verified by inspecting the corresponding LED on the module board. LED "on" represents "1" for the logic table; LED "off" represents "0" for the logic table.

| Logic Table | SOP |
| --- | --- |
| (000101) | State 1 |
| (001101) | State 2 |
| (011101) | State 3 |
| (011100) | State 4 |
| (111101) | State 5 |
| (111011) | State 6 |

In the above logic table, the bit order is bit 1 to bit 6 from far left to far right. When this logic table is used, states [1, 3], [2, 5] and [4, 6] form orthogonal state pairs. The logic table presented here is not unique for controlling the 6-rotator device under test and is one of many combinations that can generate 6 distinctive states. There are 64 combinations for 6-bit binary TTL code but only 6 distinctive polarization states. Therefore, many output SOP are degenerate or nearly degenerate among 64 combinations. A different logic table can be obtained by monitoring output polarization states on a polarization analyzer.

Next, the control program and test TTL signals are launched according to the logic table. Check whether the 6 green LEDs located on the PSG-6S board are blinking when inputting TTL control signals to the module. The blinking LED indicates that logic highs (LED on) and lows (LED off) are successfully sent to the module from the controller. Otherwise check the connection to make sure that the computer and the module are correctly connected. The optical signal from the laser source is directed into the device from the proper input to the proper output because this device is unidirectional as a polarization state generator. The SOP values are then controlled according to the above logic table to measure the optical insertion loss, switching state dependent loss, and switching transient loss.

The insertion loss without connector was measured during device fabrication. A polarization controller was used to align the output polarization state along the transmission axis of the polarizer P. The measured values for the insertion loss of the 4-rotator and 6-rotator devices tested at the light wavelength of 1550 nm are 0.83 dB in comparison to a theoretical value of 0.65 dB and 0.90 dB in comparison to a theoretical value of 0.75 dB, respectively.

The SOP dependent loss was measured by recording the optical power at different output SOP. Before the measurement, the switch time for each rotator was set at 1 second so that the a stable power reading can be obtained. The difference between the maximum and the minimum readings was used as the SOP dependent insertion loss and was 0.06 dB and 0.08 dB at the light wavelength of 1550 nm for the 4-rotator and 6-rotator devices under test, respectively.

In both the 4-rotator and 6-rotator devices under test, when reversing the magnetic field applied on a MO crystal in a rotator during the action of switching, there is a brief insertion loss increase when the magnet field passes the zero field point. This loss increase is often described as switching transient loss (or simply transient loss) and can be measured with a fast photodetector and an oscilloscope. The transient loss can be expressed as $$IL_{tr} = -10 \cdot \log\left(1 - \frac{\Delta V_s}{V_{DC}}\right)$$

where $\Delta V_S$ is the magnitude of the voltage dip during the switching, $V_{DC}$ is the DC voltage output level without switching.

Figure 29:
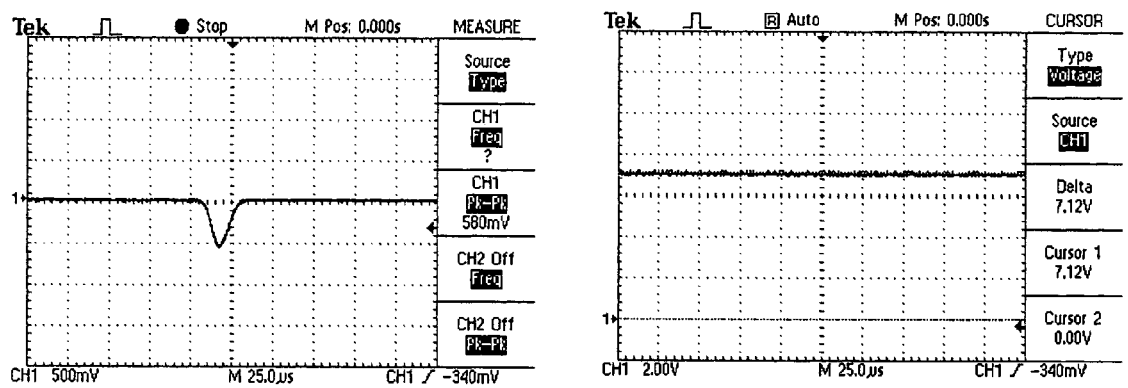
FIGS. 29, 30, 31, 32A, and 32B show measurements of actual multi-rotator devices based on the 4-rotator and 6-rotator designs.

FIG. 29 shows the measured transient loss in one MO rotator in the chart on the left and the DC voltage correspond to the total optical signal level without switching in the chart on the right. Based on the measured single stage switching $\Delta V$s (the peak-to-peak value of the Channel 1 in the chart on the left) and VDC (Cursor Delta in the chart on the right), the calculated transient loss is 0.37 dB for each stage. In a typical arbitrary 2-state switching, up to 5 stages can be switched, as evidenced by the switching from 000101 to 111011 in the above logic table.

The SOP switching time for the tested 4-rotator and 6-rotator devices was measured with a TEK210 digital oscilloscope. The switching time includes two main contributions: a switch delay of about 100 μs and a rise time of about 50 μs.

An ideal SOP generator should generate distinctive polarization states uniformly distributed on Poincare sphere and separated by 90 degrees for the angles between any two distinctive SOP. In actual device, the SOP accuracy may be limited by a number of device limitations, e.g., the switching angle of the MO crystals. The MO crystal rotation angle is a function of crystal thickness, optical wavelength, environment temperature, and crystal orientation. When crystal thickness and orientation are well controlled and uniform (such as from the same fabrication lot), the absolute SOP accuracy depends mainly on the optical wavelength and environment temperature.

Figure 30:
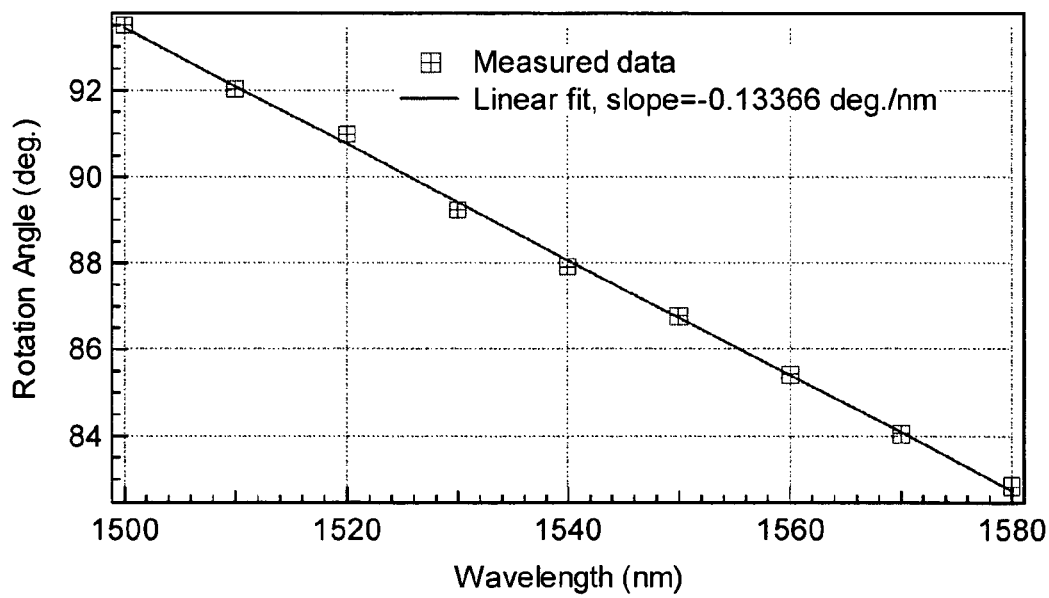

FIG. 30 shows the measured wavelength dependence of the rotation angle on Poincare sphere for the tested 6-rotator device. The actual physical rotation angle will be half of those measured on Poincare sphere. Therefore, the actual slope of the MO crystal wavelength dependence is −0.0668 deg./nm, within 2% of the manufacturer supplied data (−0.068 deg./nm).

Figure 31:
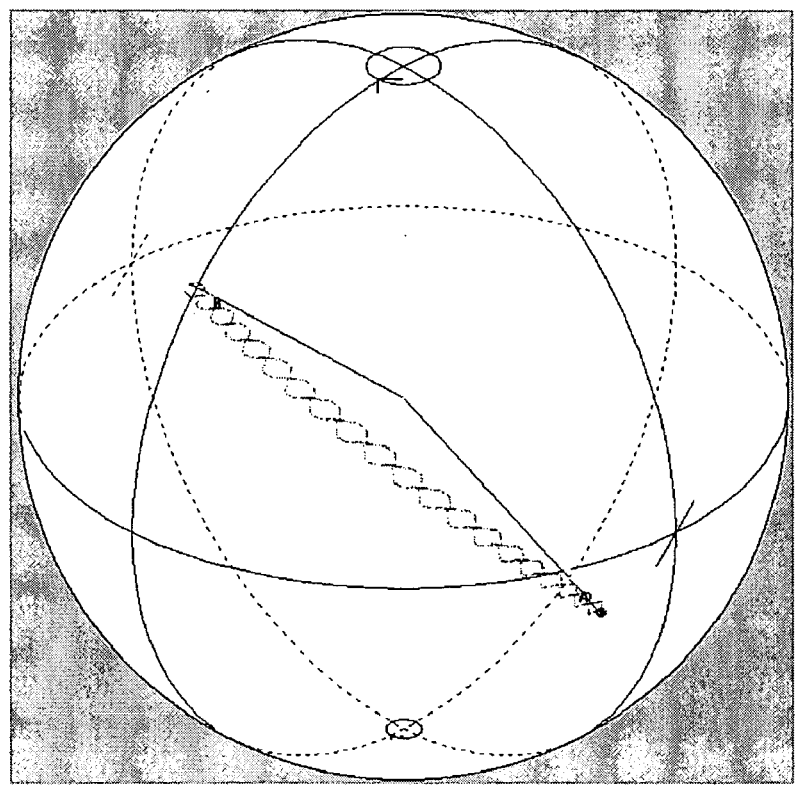

Another performance parameter for the SOP generators is the repeatability of the SOPs generated. The SOP generation repeatability for the tested 6-rotator device was measured by switching the device between two arbitrary SOPs repetitively. A typical switching trace between two SOPs for 100 times is shown in FIG. 31. The spots representing starting and ending states remain as two very clearly defined dots which indicating good SOP repeatability of the tested device. FIG. 31 also shows that the switching from SA to SB and from SB to SA do not follow the same trace and have two different traces that are interwoven together.

Figure 32A:
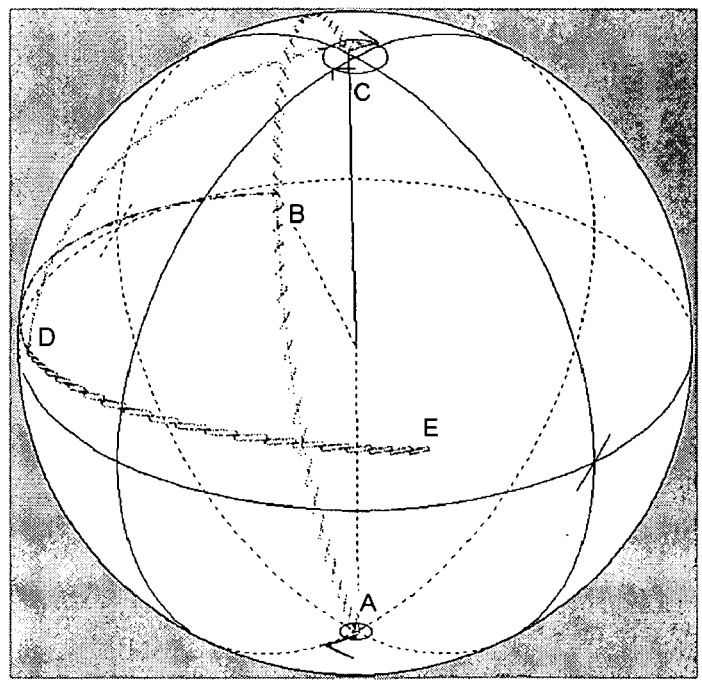
Figure 32B:
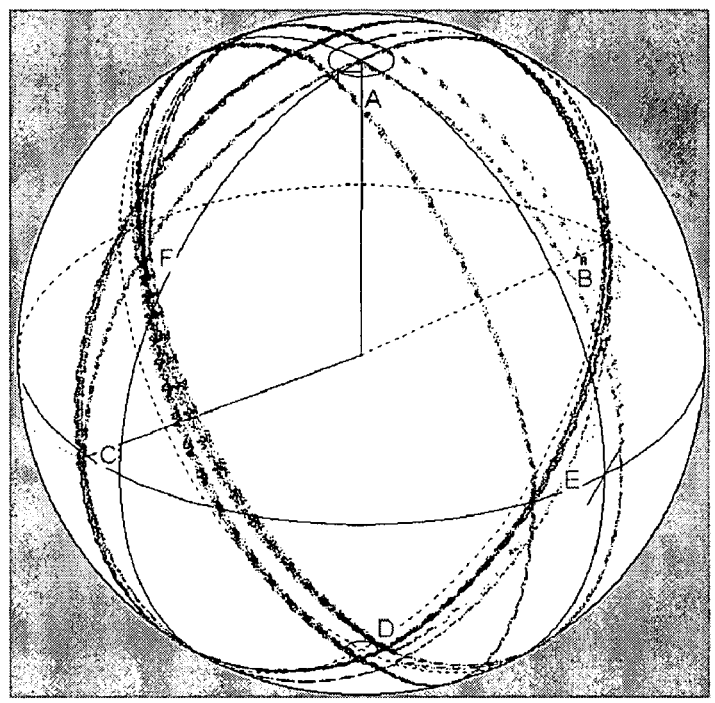

Referring back to TABLE 5, an ideal 4-rotator device can generate 5 distinctive polarization states. In our test on the SOP coverage, all 64 binary states that were available from the driver card were used to drive both the rotators in both 4-rotator and 6-rotator devices. FIGS. 32A and 32B show snap shots of the Poincare sphere for the SOPs in the 4-rotator and 6-rotator devices, respectively. In FIG. 32A, the 5 distinctive polarization states from a tested 4-rotator device are marked on the sphere. It is noticeable that near SOP A and C, there are a few other states that is very close to A and C. There is no clear explanation why these states do not overlap at the points A and C. FIG. 32B shows the 6 distinctive SOPs as states A–F on the Poincare sphere from a tested 6-rotator device. The states B, C, and F have small spreading, while the states A, D, and E have a few nearly degenerated states depending on the initial and final switching states. Comparing FIGS. 32A and 32B, it is obvious that the 4-rotator device provides only partial coverage on the Poincare sphere (i.e., one half of the sphere), while the 6-rotator device provides a symmetrical coverage on the entire Poincare sphere and thus more accurate measurements.

The above multi-rotator SOP generator may be used for both generating distinctive SOPs and analyzing SOP of input light. In certain applications, the polarization properties of optical elements, devices, modules and birefringent materials may be measured in an optical system where a multi-rotator SOP generator (i.e., a polarization state generator or PSG) is used to generate probe ling with distinctive SOPs to illuminate the device or sample under test and a SOP analyzer or polarimeter (i.e., a polarization state analyzer or PSA) using another multi-rotator SOP generator to measure the output light from the device or sample under test. Since the input SOP and the output SOP are known in this system, the polarization parameters for the device or sample under test can be obtained by solving the Muller matrix equation. In this system, and polarization state analyzer (PSA) can be used to analyze the birefringence properties of a sample. The PSG and PSA can be constructed with 4 or more pieces of Faraday rotators with +/−22.5 degree rotation angles. Other polarization-rotating mechanism may also be used. As an example, the rotators can also be constructed with liquid crystal cells. Basically, PSG can generate 4 distinctive states of polarization over the Poincare Sphere. As described above, PSA is simply a PSG which is optically reversed with the polarizaer at the output end and a photodetector for receiving the light. In this design, the PSA can also generate four distinctive SOPs over Poincare Sphere of a light beam, whose power is analyzed by a polarizer. Four power readings corresponding to the four SOPs can uniquely determine the SOP of the incoming beam.

Figure 33:
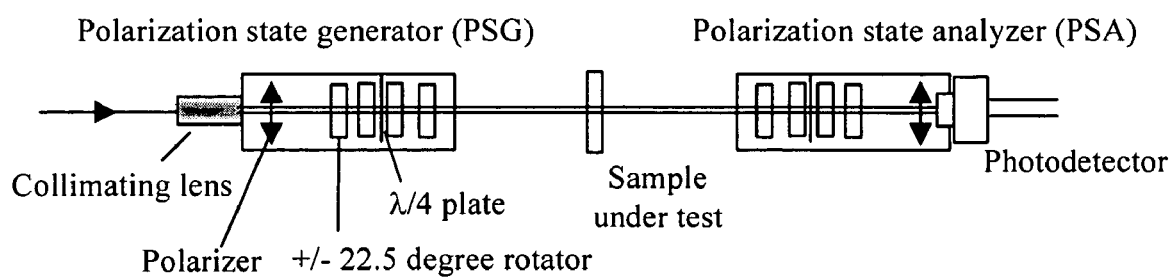
FIG. 33 shows an example of a system for measuring polarization property of a sample or device using a multi-rotator SOG generator and a separate multi-rotator polarimeter.
Figure 34A:
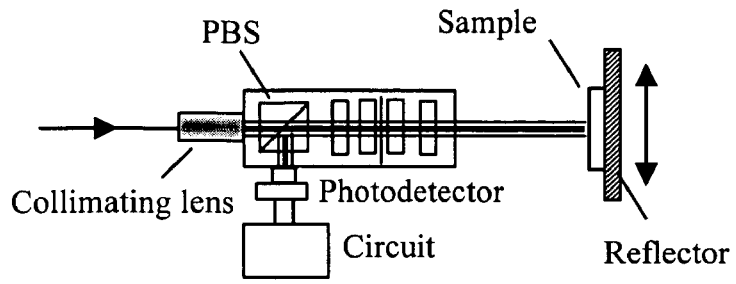
FIGS. 34A, 34B, 35, and 36 show examples of systems for measuring polarization property of a sample or device based on a folded design that uses a single set of multiple rotators for both generating SOPs and analyzing the output from the sample or device due to optical reflection.
Figure 34B:
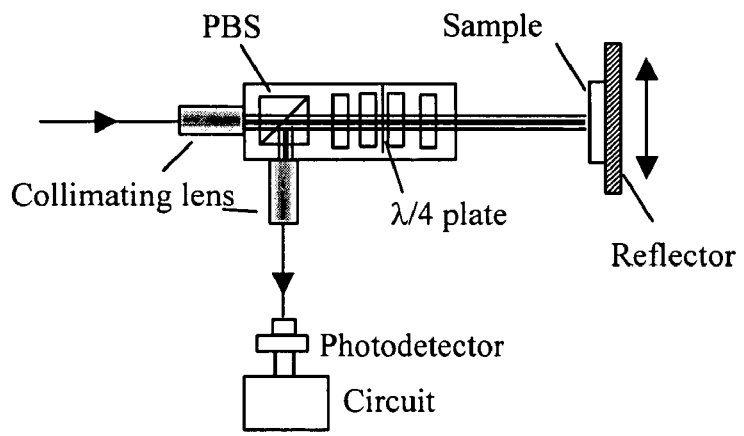

FIG. 33 illustrates one example of such a system for measuring a sample or an optical device. A holder is provided to hold the sample or device under test. A reflector is placed in the back of the sample or device to reflect light transmitted through the sample or device back. In the PSG, a linear input polarization is used to control the input polarization. Notably, when the PSG and PSA are based on the same multi-rotator design, the PSA is essentially the mirror image of the PSG. Therefore, a mirror or reflector may be used at the sample or device under test to direct the light that transmits through the sample back to the sample and the PSG in the reversed direction for SOP detection without needing a separate PSA. Such a SOP system may be viewed as a "folded" system by folding the system in FIG. 33.

Such a folded system has a number of advantages. For example, only one PSA device, such as the 4-rotator or 6-rotator PSG, is used in the folded system and thus the system is simplified and the cost is reduced. As another example, the relative SOP errors can be significantly reduced or eliminated in a folded system in comparison with the unfolded system in FIG. 33 because both the generator and the analyzer experience the exactly the same imperfections or offsets. Also, the folded system has easier sample placement than the unfolded system in FIG. 33, especially for mounting samples on a x-y translation stage. Furthermore, the probe light travels through the sample twice in the folded system and effectuates a two-fold increase in the sample interaction thickness to improve the measurement and the signal to noise ratio. The folded system also has a compact design than the unfolded system in FIG. 33 and may be suitable for various portable applications.

Figure 35:
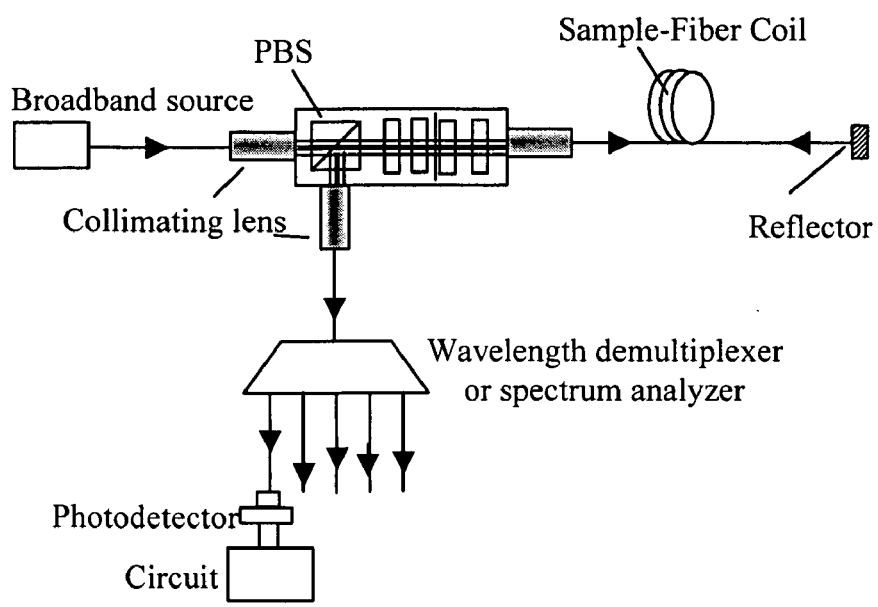
Figure 36:
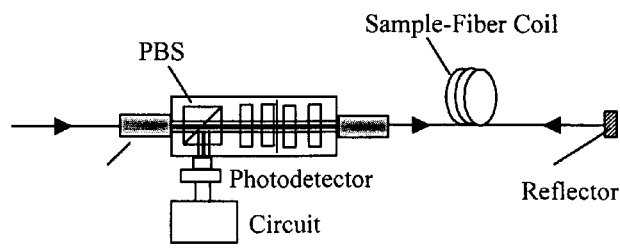

FIGS. 34A, 34B, 35, and 36 show examples of folded systems. In each example, a polarization beam splitter (PBS) is used as the input polarizer along one direction for the SOP generation and the output polarizer along an orthogonal direction for the SOP analyzing operation. The sample or the device under test may be measured at a single optical wavelength or at multiple optical wavelengths as illustrated in FIG. 35. A broadband light source is used in FIG. 35 to produce input light at different wavelengths. Alternatively, different single-wavelength light sources may be used to produce light at different wavelengths and the beams at different wavelengths are combined and sent into the system. In detection, the output light may be spectrally separated by optical filtering, e.g., using a wavelength demultiplexer or a spectrum analyzer. Output beams at different wavelengths are then received and detected by different optical detectors. Therefore, the polarization properties of the sample or device under test at different wavelengths can be simultaneously measured.

The above and other folded systems described here may be used for various applications, including compact birefringence analyzers, portable sugar content analyzers for fruit, sugar cane, and kidney diseases (sugar is optically active and rotate SOP and the amount of SOP rotation relates to sugar content), and optical window birefringence analysis.

Figure 37A:
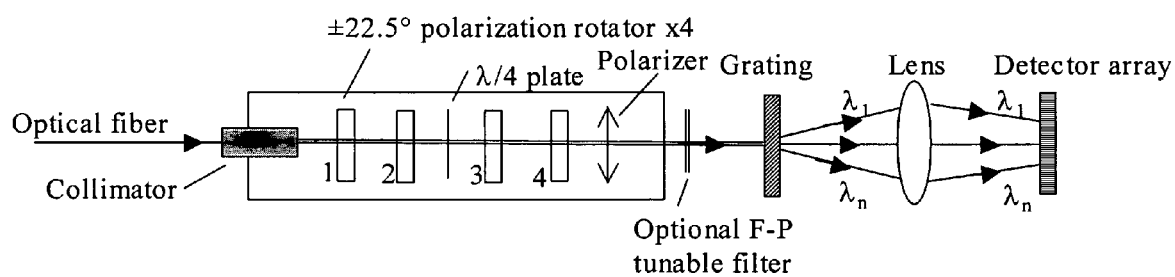
FIGS. 37A and 37B show two examples of multichannel SOP analyzers.
Figure 37B:
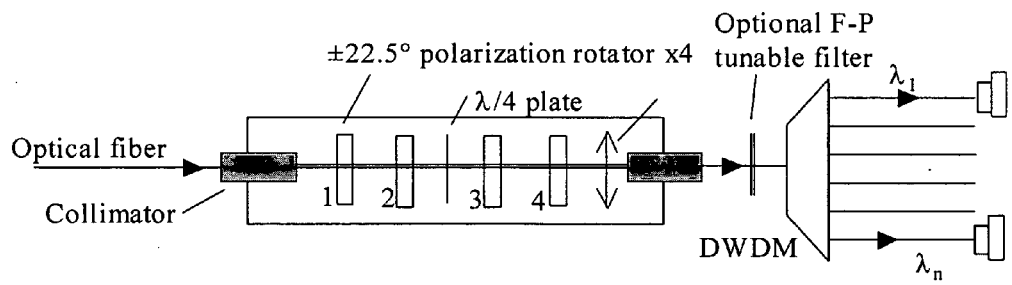

FIGS. 37A and 37B show two examples of multi-wavelength polarization analyzers with 4 or more polarization rotators. Such systems may be used in WDM applications for simultaneous multichannel measurements.

FIG. 37A shows a use of an optical diffraction grating and a lens to separate light at different wavelengths. The light passing through the polarizer is separated in wavelength by the diffraction grating and then is focused by a lens to different locations on a photodetector array. Analyzing the optical power in different channels can obtain the SOP, DOP, PMD information of each channel. Similarly, in FIG. 37B, the incoming light containing all different channels are separated by a WDM or dense WDM channel demultiplexer after passing through the polarizer. The optical power levels in each channel for different SOP states are then monitored and used to obtain complete information of SOP, DOP, and PMD of each channel.

Figure 38:
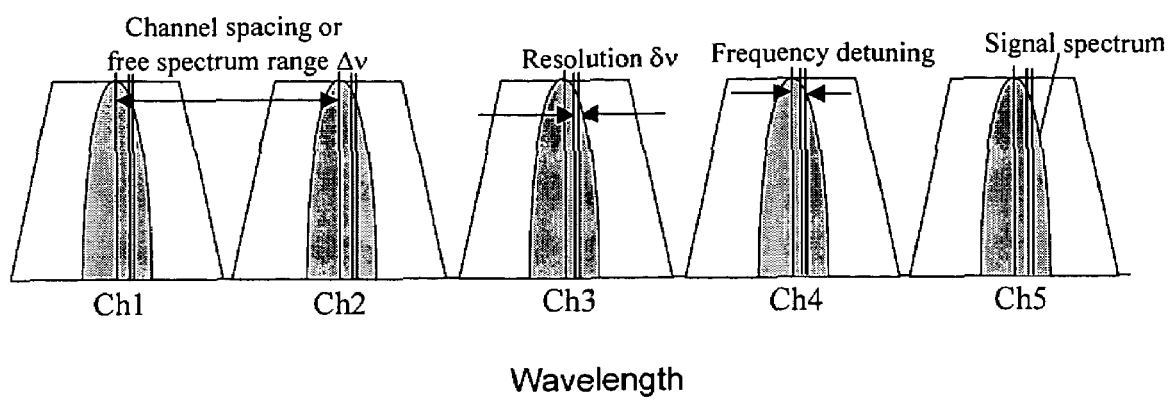
FIG. 38 illustrates operation of the multichannel SOP analyzers in FIGS. 37A and 37B.

To improve the spectrum resolution, a tunable Fabry-Perot filter can be used to filter the output of the output polarizer before the light is spectrally separated by the grating and the lens or the demultiplexer. The free spectrum range of the tunable filter may be the same as that of the channel spacing of the multiwavelength channels in the WDM or DWDM signals. For example, for a DWDM system of 100 GHz spacing, the free spectrum range (FSR) of the filter is also chosen to be 100 GHz. The resolution increases with the finesse (F) of the filter. For example, a finesse of 100 in a Fabry-Perot filter corresponds to a spectrum resolution is 1 GHz. For a finesse of 1000, the spectrum resolution is 0.1 GHz. For a 10 Gb/s signal, the bandwidth is about 10 GHz. Scanning the F-P filter across the signal spectrum and measuring the SOP of each frequency components yield the value of fiber's differential group delay (DGD) and the direction of fiber's principle state of polarization (PSP). FIG. 38 illustrates the operations of such a multichannel analyzer.

In the absence of depolarization, the optical signal to noise ratio (OSNR) directly relates to DOP of each channel: OSNR=DOP/(1−DOP). Therefore, the device can be used as a performance monitor for the spectrum, OSNR, SOP, DOP, and PSP of each channel. Because of the extremely high spectral resolution, the OSNR can also be directly measured by scanning the F-P filter across the channel. The minimum detected power in each scan corresponds to the noise power $p_n$ (ν) in each channel. The signal power $p_s$ (ν) at each frequency ν is the measured power p(ν) minus the noise power $p_n$ (ν):

$$p_s(v) = p(v) - p_n(v)$$

$$OSNR = \frac{\int_{-\Delta}^{\Delta} p(v) - p_n(v)}{\int_{-\Delta}^{\Delta} p_n(v)}$$

In the absence of depolarization, the OSNR results from the DOP measurement and from the spectrum scan measurement should be identical. Therefore, a calibration factor between the two measurement can be obtained by using a short fiber with negligible DGD.

In the presence of PMD (depolarization), the DOP can be expressed as:

$$DOP = \frac{P_{pol}}{P_{pol} + P_{nonpol}} = \frac{(1-\delta)P_s}{P_s + P_n}$$

where Ps and Pn are the signal and noise powers of a given bandwidth and δ is the depolarization factor which is 0 if the signal has no depolarization and is 1 if the signal is totally depolarized. The OSNR is related to DOP by:

$$SNR = P_s/P_n = \frac{DOP}{1 - \delta - DOP}$$

Therefore, with both the independent DOP and OSNR measurements, the depolarization factor can be calculated:

δ=1−*DOP*−*DOP/SNR*

The SOP generator described here can be used to replace the rotating quarter wave and polarizer assembly shown in FIGS. 13, 14, and 15 on multichannel polarimeter/polarization analyzers. Other applications of such SOP generator may also be possible.

Only a few examples and implementations are described. However, other implementations, variations, modifications, and enhancements are possible.

What is claimed is:
1. A device, comprising:
first and second polarization rotators sequentially positioned in an optical path;
a quarter waveplate in said optical path to receive output light from said first and said second polarization rotators; and
third and fourth polarization rotators sequentially positioned in said optical path to receive output light from said quarter waveplate, wherein each polarization rotator is adjustable in response to a control signal.

2. The device as in claim 1, further comprising an input optical polarizer in said optical path in front of said first and said second polarization rotators to filter input light and to direct the filtered input through said first and said second polarization rotators, said quarter wave plate, and third and fourth polarization rotators.

3. The device as in claim 1, wherein each polarization rotator is a magneto-optic (MO) rotator.

4. The device as in claim 1, wherein each rotator is responsive to a first control signal to rotate the polarization by +22.5°, and responsive to a second control signal to rotate the polarization by −22.5°.

5. The device as in claim 4, wherein said rotators are aligned with respect to one another so that said first and said second rotators are rotated in the same direction to produce a net rotation of 45°, and said third and said fourth rotators are rotated in the same direction to produce a net rotation of 45°, and said first and said second rotators are rotated in the opposite directions to produce a net rotation of 0°, and said third and said fourth rotators are rotated in the opposite directions to produce a net rotation of 0°.

6. The device as in claim 1, further comprising:
an output optical polarizer in said optical path to receive and filter light that transmits through said first and said second polarization rotators, said quarter wave plate, and third and fourth polarization rotators; and
an optical detector positioned to receive the filtered light from said output optical polarizer.

7. The device as in claim 6, further comprising:
an optical grating positioned between said output optical polarizer and said optical detector and operable to separate light of different wavelengths into different directions; and
a lens positioned to direct light of different wavelengths from said optical grating into different locations on said optical detector, respectively.

8. The device as in claim 7, further comprising a tunable Fabry-Perot filter located between said output optical polarizer and said optical grating to filter light.

9. The device as in claim 7, wherein said optical detector is a detector array.

10. The device as in claim 6, further comprising a wavelength demultiplexer which separates light of different wavelengths into separate beams.

11. The device as in claim 10, further comprising a tunable Fabry-Perot filter located between said output optical polarizer and said wavelength demultiplexer to filter light.

12. The device as in claim 1, further comprising fifth and sixth polarization rotators sequentially positioned in said optical path, wherein each of said fifth and sixth polarization rotators is adjustable in response to a control signal.

13. The device as in claim 12, wherein each rotator is responsive to a first control signal to rotate the polarization by +22.5°, and responsive to a second control signal to rotate the polarization by −22.5°.

14. The device as in claim 12, further comprising:
an output optical polarizer in said optical path to receive and filter light that transmits through each of said first, said second, said third, said fourth, said fifth, and said sixth polarization rotators, and said quarter wave plate; and
an optical detector positioned to receive the filtered light from said output optical polarizer.

15. The device as in claim 1, further comprising:
a polarization beam splitter positioned in front of said first polarization rotator to transmit input light in a first polarization to said first polarization rotator and to reflect light in a second polarization orthogonal to said first polarization that is from said first polarization rotator to produce an output beam;
a sample holder located in said optical path after said fourth polarization rotator to hold a sample which receives light that transmits through said fourth polarization rotator;
a reflector located in said optical path to reflect light transmitted through said fourth polarization rotator and the sample back to the sample and said fourth polarization rotator; and
an optical detector located to receive said output beam from said polarization beam splitter.

16. The device as in claim 15, further comprising an optical device between said polarization beam splitter and said optical detector and operable to separate light of different wavelengths in said output beam into separate beams.

17. A device, comprising:
at least four polarization rotators positioned in an optical path, each polarization rotator being adjustable in response to a control signal to rotate the polarization by either +22.5° or −22.5°; and
a quarter wave plate in said optical path.

18. The device as in claim 17, further comprising six polarization rotators.

19. The device as in claim 17, wherein each polarization rotator is a magneto-optic (MO) rotator.

20. The device as in claim 17, wherein each polarization rotator is a liquid crystal element.

21. A method, comprising:
using at least four polarization rotators and a quarter wave plate in an optical path to transmit light;
controlling each polarization rotator to rotate polarization by two different predetermined angles; and
controlling the at least four polarization rotators to operate in different rotator settings and to generate at least four different states of polarization.

22. The method as in claim 21, wherein the two different predetermined angels are +22.5° and −22.5°, respectively.

23. The method as in claim 21, further comprising:
directing light in the at least four different states of polarization to transmit through a sample whose polarization property is to be measured;
measuring corresponding output states of polarization of transmitted light of the sample; and
using the at least four different states of polarization of light entering the sample and the corresponding output states of polarization to determine the polarization property of the sample.

24. The method as in claim 23, further comprising:
using at least another four polarization rotators and another quarter wave plate positioned in an optical path of the light transmitted through the sample;
controlling the at least another four polarization rotators to at least four different rotator settings which generate at least four different states of polarization; and
using a fixed linear polarizer to filter light that transmits through the at least another four polarization rotators and the other quarter wave plate;
measuring power levels of light filtered by the fixed linear polarizer; and
using the measured power levels to determine the corresponding output states of polarization of light that transmits through the sample.

25. The method as in claim 23, further comprising:
directing light in the at least four different states of polarization to transmit through a sample whose polarization property is to be measured;
reflecting light back to transmit through the sample and the at least four polarization rotators and the quarter wave plate as a reflected light beam;
measuring power levels of the reflected light beam at a fixed output polarization; and
using the measured power levels to determine the corresponding output states of polarization of light that transmits through the sample.

26. The method as in claim 21, further comprising:
directing a beam of a unknown state of polarization into the optical path to transmit through the at least four polarization rotators and the quarter wave plate;
controlling the at least four polarization rotators to operate in the different rotator settings that generate at least four different states of polarization to control polarization of the beam;
directing the beam through a fixed polarizer;
measuring power levels of light transmitted through the fixed polarizer under the different rotator settings; and
using the measured power levels and the different rotator settings to determine the state of polarization of the beam.

27. The method as in claim 26, further comprising using the determined state of polarization of the beam to determine a degree of polarization of the beam.

28. The method as in claim 26, further comprising using the determined state of polarization of the beam to determine a signal to noise ratio the beam.

* * * * *